(12) United States Patent
Kruck et al.

(10) Patent No.: US 11,766,396 B2
(45) Date of Patent: Sep. 26, 2023

(54) KIT AND METHOD FOR DYEING KERATINOUS MATERIAL BY MEANS OF AMINOSILICONE AND A CHROMOPHORIC COMPOUND

(71) Applicant: Henkel AG & Co. KGaA, Duesseldorf (DE)

(72) Inventors: Constanze Kruck, Grevenbroich (DE); Sandra Hilbig, Bochum (DE); Daniela Kessler-Becker, Leverkusen (DE); Melanie Moch, Dormagen (DE); Susanne Dickhof, Viersen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 17/763,177

(22) PCT Filed: Jul. 13, 2020

(86) PCT No.: PCT/EP2020/069716
§ 371 (c)(1),
(2) Date: Mar. 23, 2022

(87) PCT Pub. No.: WO2021/058157
PCT Pub. Date: Apr. 1, 2021

(65) Prior Publication Data
US 2022/0347079 A1 Nov. 3, 2022

(30) Foreign Application Priority Data
Sep. 23, 2019 (DE) .................. 102019214469.1

(51) Int. Cl.
*A61Q 5/10* (2006.01)
*A61K 8/898* (2006.01)
*A61K 8/24* (2006.01)
*A61K 8/362* (2006.01)
*A61K 8/49* (2006.01)

(52) U.S. Cl.
CPC .............. *A61K 8/898* (2013.01); *A61K 8/24* (2013.01); *A61K 8/362* (2013.01); *A61K 8/494* (2013.01); *A61Q 5/10* (2013.01); *A61K 2800/43* (2013.01); *A61K 2800/882* (2013.01)

(58) Field of Classification Search
CPC .......... A61K 8/898; A61K 8/24; A61K 8/362; A61K 8/494; A61K 2800/43; A61K 2800/882; A61K 2800/87; A61K 8/36; A61K 8/19; A61K 8/26; A61Q 5/10; A61Q 5/065; A61Q 5/06
USPC .............................................. 8/405
See application file for complete search history.

(56) References Cited

U.S. PATENT DOCUMENTS

| 2017/0172901 A1* | 6/2017 | Kerl | ............ | A61K 8/22 |
| 2017/0239152 A1* | 8/2017 | Goutsis | ............ | A61K 8/24 |

FOREIGN PATENT DOCUMENTS

| WO | 2009027237 A2 | 3/2009 |
| WO | 2015090804 A1 | 6/2015 |
| WO | 2019174823 A1 | 9/2019 |

* cited by examiner

*Primary Examiner* — Eisa B Elhilo
(74) *Attorney, Agent, or Firm* — Lorenz & Kopf, LLP

(57) ABSTRACT

The objective of the present disclosure is a multi-component packaging unit (kit-of-parts) for dyeing keratinous material, in particular human hair, comprising separately prepared
  a first container comprising an agent (a), wherein the agent comprises (a):
  (a1) at least one amino-functionalized silicone polymer, and
a second container comprising an agent (b), wherein the agent comprises (b):
  (b1) Water and
  (b2) a buffer system comprising at least one inorganic or organic acid (b2-I) and at least one salt of this acid (b2-II), and
  (b3) at least one color-imparting compound.
A second objective of the present disclosure is a corresponding method in which the two agents (a) and (b) are used.

20 Claims, No Drawings

KIT AND METHOD FOR DYEING KERATINOUS MATERIAL BY MEANS OF AMINOSILICONE AND A CHROMOPHORIC COMPOUND

CROSS-REFERENCE TO RELATED APPLICATION

This application is a U.S. National-Stage entry under 35 U.S.C. § 371 based on International Application No. PCT/EP2020/069716, filed Jul. 13, 2020, which was published under PCT Article 21(2) and which claims priority to German Application No. 102019214469.1, filed Sep. 23, 2019, which are all hereby incorporated in their entirety by reference.

TECHNICAL FIELD

The subject of the present application is a multi-component packaging unit (kit-of-parts) for dyeing keratinous material, in particular human hair, which comprises at least two different agents (a) and (b) in separately prepared containers. The agent (a) comprises at least one amino-functionalized silicone polymer (a1). The agent (b) comprises water (b1), a buffer system (b2) of at least one inorganic or organic acid (b2-I) and at least one salt of this acid (b2-II) and
(b3) comprises at least one color-imparting compound. This coloring compound is very preferably a pigment.

A second subject matter of this application is a method of dyeing keratinous material using the two agents (a) and (b) described above.

BACKGROUND

Changing the shape and color of keratinous material, especially human hair, is a key area of modern cosmetics. To change the hair color, the expert knows various coloring systems depending on the coloring requirements. Oxidation dyes are usually used for permanent, intensive dyeings with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes have very long-lasting dyeing results.

When direct dyes are used, ready-made dyes diffuse from the colorant into the hair fiber. Compared to oxidative hair dyeing, the dyeings obtained with direct dyes have a shorter shelf life and quicker wash ability. Dyes with direct dyes usually remain on the hair for a period of between 5 and 20 washes.

The use of color pigments is known for short-term color changes on the hair and/or skin. Color pigments are understood to be insoluble, coloring substances. These are present undissolved in the dye formulation in the form of small particles and are only deposited from the outside on the hair fibers and/or the skin surface. Therefore, they can usually be removed again without residue by a few washes with detergents comprising surfactants. Various products of this type are available on the market under the name hair mascara.

The advantage of a hair mascara product is that the colorant compounds, such as pigments, are deposited only in the form of a film on the surface of the keratin fiber. The nature of the keratin fiber itself is thus not changed during the application of the product, so that the use of a hair mascara product is associated with particularly low hair damage. If the user wishes to return to his original hair color, the dye can be removed from the keratin fiber quickly, completely and without residue, without damaging the fibers or changing the original hair color. The development of pigment-based keratin colorants is therefore fully in line with the trend.

In the work leading to the present disclosure, it has been found that coloring compounds, and in particular pigments, can tend to become unstable after long storage times in the formulation. As has been observed, these instabilities occur when the pigments have been stored in alkaline environments. As a result, the color result obtained after application on the keratin material may be different than desired. For this reason, there is still a need for optimization of pigment-based coloring systems, with the storage stability of the formulations and the color intensities obtained with stored formulations in particular requiring improvement.

Furthermore, it has also been known for a long time to the expert that the pH value of a hair dye can have a massive influence on the intensity and the nuance loss of the coloration. As the work leading to this present disclosure has shown, this influence also occurs with pigment-based coloring systems. This influence of the pH value on the color result can prove to be problematic, since the user wants to dye his hair in exactly the color that is also indicated on the packaging of the dye. Achieving predictable color results with reproducible color intensity is therefore essential for the user.

BRIEF SUMMARY

Multicomponent packaging units and processes for dyeing keratinous material are provided herein. In an embodiment, a multicomponent packaging unit for coloring keratinous material comprises, separately assembled:
a first container comprising an agent (a), wherein the agent (a) comprises:
  (a1) at least one amino-functionalized silicone polymer, and
a second container containing an agent (b), wherein the agent (b) comprises:
  (b1) water and
  (b2) a buffer system comprising at least one inorganic or organic acid (b2-I) and at least one salt of the inorganic or organic acid (b2-II), and
  (b3) at least one color-imparting compound.

In another embodiment, a process for dyeing keratinous material comprises the following steps:
(1) Providing an agent (a), wherein the agent (a) comprises:
  (a1) at least one amino-functionalized silicone polymer, and
(2) Providing an agent (b), wherein the agent (b) comprises:
  (b1) water and
  (b2) a buffer system comprising at least one inorganic or organic acid (b2-I) and at least one salt of the inorganic or organic acid (b2-II), and
  (b3) at least one colorant compound,
(3) Preparing an application mixture by mixing agents (a) and (b),
(4) Applying the application mixture prepared in step (3) to the keratinous material,
(5) Exposing the application mixture applied in step (4) to the keratinous material; and
(6) Rising the application mixture with water.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description. It is to be appreciated that all values as provided herein, save for the actual examples, are approximate values with endpoints or particular values intended to be read as "about" or "approximately" the value as recited.

It has been the object of the present disclosure to provide a staining system having fastness properties comparable to oxidative staining, if possible. Wash fastness properties should be outstanding, but the use of oxidation dye precursors normally used for this purpose should be avoided. A technology was sought that would make it possible to fix the colorant compounds (especially pigments) known from the prior art to the hair in an extremely durable manner. When the agents are used in a dyeing process, intensive dyeing results with good fastness properties should be obtained. A particular focus of the task was to achieve storage-stable formulations that can be used to achieve a precisely defined, intensive color result without undesirable color shifts, regardless of the period over which they are stored. In addition, the stains obtained should have particularly good reproducibility.

Surprisingly, it has now been found that the task can be excellently solved if keratinous materials, in particular hair, are dyed with the aid of a multicomponent packaging unit (kit-of-parts) comprising at least two agents (a) and (b) separately packaged in different containers. Here, the agent (a) comprises at least one amino-functionalized silicone polymer (a1). The agent (b) comprises water (b1), furthermore a buffer system (b2) of at least one inorganic or organic acid (b2-I) and at least one salt of this acid (b2-II), and additionally at least one colorant compound (b3), which is particularly preferably a pigment.

A first object of the present disclosure is a multi-component packaging unit (kit-of-parts) for dyeing keratinous material, in particular human hair, comprising separately prepared a first container comprising an agent (a), wherein the agent comprises (a):
(a1) at least one amino-functionalized silicone polymer, and a second container comprising an agent (b), wherein the agent comprises (b):
(b1) Water and
(b2) a buffer system comprising at least one inorganic or organic acid (b2-I) and at least one salt of this acid (b2-II), and
(b3) at least one color-imparting compound.

The multicomponent packaging unit comprises at least the two agents (a) and (b), these are mixed before use. The application mixture prepared by mixing agents (a) and (b) is then applied to the keratin material, allowed to act and then rinsed out again with water.

Surprisingly, the work leading to the present disclosure has shown that the color shifts that can occur after storage of the coloring compounds or pigments in the formulation were effectively prevented when the coloring compound, especially pigment (b3), and the amino-functionalized silicone polymer (a1) were not incorporated together in one formulation, but separately in different formulations. Particularly well reproducible color results could be obtained when the agent (b) with the color-imparting compounds (b3) included a buffer system (b2) of at least one inorganic or organic acid (b2-I) and at least one salt of this acid (b2-II) in a water-comprising carrier (b1).

Keratinic Material

Keratinous material includes hair, skin, nails (such as fingernails and/or toenails). Wool, furs and feathers also fall under the definition of keratinous material. Preferably, keratinous material is understood to be human hair, human skin and human nails, especially fingernails and toenails. Keratinous material is understood to be human hair.

Agent (a)

In a first container, the multi-component packaging unit as contemplated herein comprises agent (a). The container can be, for example, a sachet, a bottle, a can, a jar or also another container suitable for cosmetic formulations. Agent (a) is exemplified by its content of the essential constituent of the present disclosure (a1).

Amino Functionalized Silicone Polymer (a1) in the Agent (a)

As an ingredient (a1) essential to the present disclosure, the agent (a) comprises at least one amino-functionalized silicone polymer. The amino-functionalized silicone polymer may alternatively be referred to as amino silicone or amodimethicone.

Silicone polymers are macromolecules with a molecular weight of at least 500 g/mol, preferably at least 1000 g/mol, more preferably at least 2500 g/mol, particularly preferably at least 5000 g/mol, which comprise repeating organic units.

The maximum molecular weight of the silicone polymer depends on the degree of polymerization (number of polymerized monomers) and the batch size and is also partly determined by the polymerization method. For the purposes of the present disclosure, it is preferred if the maximum molecular weight of the silicone polymer is not more than $10^7$ g/mol, preferably not more than $10^6$ g/mol, and particularly preferably not more than $10^5$ g/mol.

The silicone polymers comprise many Si—O repeating units, and the Si atoms may carry organic radicals such as alkyl groups or substituted alkyl groups. Alternatively, a silicone polymer is therefore also referred to as polydimethylsiloxane.

Corresponding to the high molecular weight of silicone polymers, these are based on more than 10 Si—O repeat units, preferably more than 50 Si—O repeat units, and more preferably more than 100 Si—O repeat units, most preferably more than 500 Si—O repeat units.

An amino-functionalized silicone polymer is understood to be a functionalized silicone that carries at least one structural unit with an amino group. Preferably, the amino-functionalized silicone polymer carries multiple structural units, each having at least one amino group. An amino group is understood to mean a primary amino group, a secondary amino group and a tertiary amino group. All these amino groups can be protonated in the acidic environment and are then present in their cationic form.

In principle, beneficial effects could be obtained with amino-functionalized silicone polymers (a1) if they carry at least one primary, at least one secondary and/or at least one tertiary amino group. However, intense colorations with the best wash fastness were obtained when an amino-functionalized silicone polymer (a1) was used in agent (a), which comprises at least one secondary amino group.

In a very particularly preferred embodiment, the agent (a) comprises at least one amino-functionalized silicone polymer (a1) having at least one secondary amino group.

The secondary amino group(s) may be located at various positions on the amino-functionalized silicone polymer. Particularly beneficial effects were found when an amino-functionalized silicone polymer (a1) was used that has at least one, preferably several, structural units of the formula (Si amino).

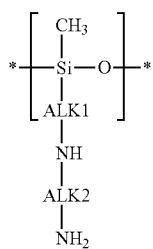
(Si-Amino)

In the structural units of the formula (Si amino), the abbreviations ALK1 and ALK2 independently stand for a linear or branched, bivalent $C_1$-$C_{20}$ alkylene group.

In another very particularly preferred embodiment, the agent (a) comprises at least one amino-functionalized silicone polymer (a1) which comprises at least one structural unit of the formula (Si amino),

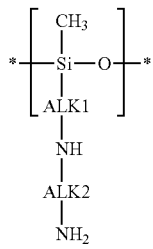
(Si-Amino)

where ALK1 and ALK2 independently represent a linear or branched $C_1$-$C_{20}$ divalent alkylene group.

The positions marked with an asterisk (*) indicate the bond to further structural units of the silicone polymer. For example, the silicon atom adjacent to the star may be bonded to another oxygen atom, and the oxygen atom adjacent to the star may be bonded to another silicon atom or even to a $C_1$-$C_6$ alkyl group.

A bivalent $C_1$-$C_{20}$ alkylene group can alternatively be referred to as a divalent or divalent $C_1$-$C_{20}$ alkylene group, by which is meant that each ALK1 or AK2 grouping can form two bonds.

In the case of ALK1, one bond occurs from the silicon atom to the ALK1 grouping, and the second bond is between ALK1 and the secondary amino group.

In the case of ALK2, one bond is from the secondary amino group to the ALK2 grouping, and the second bond is between ALK2 and the primary amino group.

Examples of a linear bivalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, bivalent alkylene groups can also be branched. Examples of branched divalent, bivalent $C_3$-$C_{20}$ alkylene groups are (—$CH_2$—$CH(CH_3)$—) and (—$CH_2$—$CH(CH_3)$—$CH_2$—).

In another particularly preferred embodiment, the structural units of the formula (Si amino) represent repeat units in the amino-functionalized silicone polymer (a1), so that the silicone polymer comprises multiple structural units of the formula (Si amino).

Particularly well-suited amino-functionalized silicone polymers (a1) with at least one secondary amino group are listed below.

Dyeings with the best wash fastnesses could be obtained when the multicomponent packaging unit as contemplated herein comprises an agent (a) comprising at least one amino-functionalized silicone polymer (a1) comprising structural units of the formula (Si-I) and of the formula (Si-II)

(Si-I)

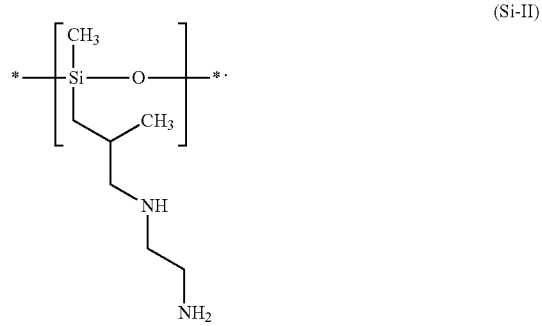
(Si-II)

In a further explicitly quite particularly preferred embodiment, the agent (a) comprises at least one amino-functionalized silicone polymer (a1) which comprises structural units of the formula (Si-I) and of the formula (Si-II)

(Si-I)

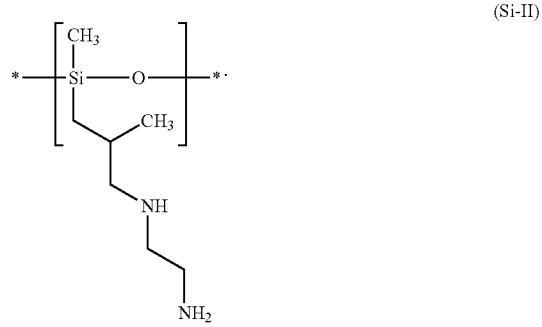
(Si-II)

A corresponding amino functionalized silicone polymer with the structural units (Si-I) and (Si-II) is, for example, the commercial product DC 2-8566 or Dowsil 2-8566 Amino Fluid, which is commercially distributed by the Dow Chemical Company and bears the designation "Siloxanes and Silicones, 3-[(2-aminoethy)pamino]-2-methylpropyl Me, Di-Me-Siloxane" and the CAS number 106842-44-8. Another particularly preferred commercial product is Dowsil AP-8658 Amino Fluid, which is also sold commercially by the Dow Chemical Company.

In a further preferred embodiment, the agent (a) comprises at least one amino-functional silicone polymer (a1) of the formula of the formula (Si-III),

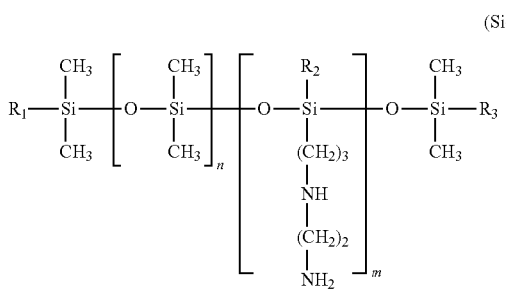

where
m and n mean numbers chosen so that the sum (n+m) is in the range 1 to 1000,
n is a number in the range 0 to 999 and m is a number in the range 1 to 1000,
R1, R2 and R3, which are the same or different, denote a hydroxy group or a C1-4 alkoxy group,
wherein at least one of R1 to R3 represents a hydroxy group;

Further kit-of-parts preferred as contemplated herein include the agent (a) that comprises at least amino-functional silicone polymer (a1) of the formula of the formula (Si-IV),

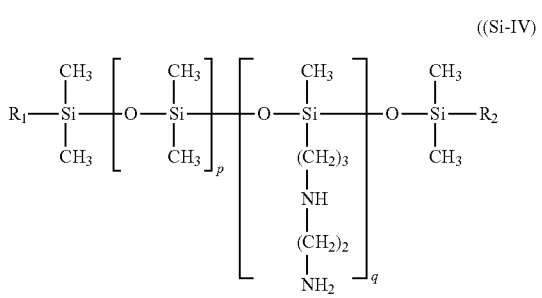

where
p and q mean numbers chosen so that the sum (p+q) is in the range 1 to 1000,
p is a number in the range 0 to 999 and q is a number in the range 1 to 1000,
R1 and R2, which are different, denote a hydroxy group or a C1-4 alkoxy group, at least one of R1 to R2 denoting a hydroxy group.

The silicones of the formulas (Si-III) and (Si-IV) differ in the grouping at the Si atom, which carries the nitrogen-comprising group: In formula (Si-III), R2 represents a hydroxy group or a C1-4 alkoxy group, while the radical in formula (Si-IV) is a methyl group. The individual Si groupings, which are marked with the indices m and n or p and q, do not have to be present as blocks; rather, the individual units can also be present in a statistically distributed manner, i.e. in the formulas (Si-III) and (Si-IV), not every R1-Si($CH_3$)$_2$ group is necessarily bonded to an —[O—Si($CH_3$)$_2$] grouping.

Kit-of-parts as contemplated herein, in which an agent (a) comprising at least one amino-functional silicone polymer (a1) of the formula of the formula (Si-V) is applied to the keratin fibers, have also proved to be particularly effective regarding the desired effects.

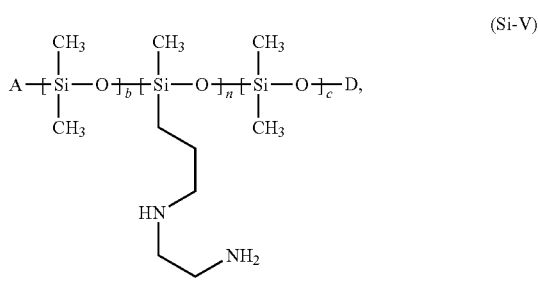

where
A represents a group —OH, —O—Si($CH_3$)$_3$, —O—Si($CH_3$)$_2$OH, —O—Si($CH_3$)$_2$OCH$_3$,
D represents a group —H, —Si($CH_3$)$_3$, —Si($CH_3$)$_2$OH, —Si($CH_3$)$_2$OCH$_3$, b, n and c stand for integers between 0 and 1000, with the specifications
n>0 and b+c>0
at least one of the conditions A=—OH or D=—H is fulfilled.

In the above formula (Si-V), the individual siloxane units are statistically distributed with the indices b, c and n, i.e., they do not necessarily have to be block copolymers.

Agent (a) may further comprise one or more different amino-functionalized silicone polymers represented by the formula (Si-VI)

where R is a hydrocarbon or a hydrocarbon radical having from 1 to about 6 carbon atoms, Q is a polar radical of the general formula —$R^1$HZ wherein $R^1$ is a divalent linking group bonded to hydrogen and the radical Z composed of carbon and hydrogen atoms, carbon, hydrogen and oxygen atoms, or carbon, hydrogen and nitrogen atoms, and Z is an organic amino functional radical comprising at least one amino functional group; "a" takes values ranging from about 0 to about 2, "b" takes values ranging from about 1 to about 3, "a"+"b" is less than or equal to 3, and "c" is a number ranging from about 1 to about 3, and x is a number ranging from 1 to about 2,000, preferably from about 3 to about 50 and most preferably from about 3 to about 25, and y is a number in the range of from about 20 to about 10,000, preferably from about 125 to about 10,000 and most preferably from about 150 to about 1,000, and M is a suitable silicone end group as known in the prior art, preferably trimethylsiloxy. Non-limiting examples of radicals represented by R include alkyl radicals, such as methyl, ethyl, propyl, isopropyl, isopropyl, butyl, isobutyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl and the like, and sulfur-comprising radicals, such as mercaptoethyl, mercaptopropyl, mercaptohexyl, mercaptophenyl and the like; preferably R is an alkyl radical comprising from 1 to about 6 carbon atoms, and most preferably R is methyl. Examples of $R^1$ include methylene, ethylene, propylene, hexamethylene, decamethylene, —$CH_2CH(CH_3)CH_2$—, phenylene, naphthylene, —$CH_2CH_2SCH_2CH_2$—, —$CH_2CH_2OCH_2$—, —$OCH_2CH_2$—, —$OCH_2CH_2CH_2$—, —$CH_2CH(CH_3)C(O)OCH_2$—, —$(CH_2)_3CC(O)OCH_2CH_2$—, —$C_6H_4C_6H_4$—, —$C_6H_4CH_2C_6H_4$—; and —$(CH_2)_3C(O)SCH_2CH_2$—.

Z is an organic amino functional radical comprising at least one amino functional group. One formula for Z is $NH(CH_2)_zNH_2$, where z is 1 or more. Another formula for Z is —$NH(CH_2)_z(CH_2)_{zz}NH$, wherein both z and zz are independently 1 or more, this structure comprising diamino ring structures, such as piperazinyl. Z is most preferably an —$NHCH_2CH_2NH_2$ radical. Another formula for Z is —$N(CH_2)_z(CH_2)_{zz}NX_2$ or —$NX_2$, wherein each X of $X_2$ is independently selected from the group of hydrogen and alkyl groups having 1 to 12 carbon atoms, and zz is 0.

Q is most preferably a polar, amine-functional radical of the formula —$CH_2CH_2CH_2NHCH_2CH_2NH_2$. In the formulas, "a" takes values ranging from about 0 to about 2, "b" takes values ranging from about 2 to about 3, "a"+"b" is less than or equal to 3, and "c" is a number ranging from about 1 to about 3. The molar ratio of $R_aQ_bSiO_{(4-a-b)/2}$ units to $R_cSiO_{(4-c)/2}$ units is in the range of about 1:2 to 1:65, preferably from about 1:5 to about 1:65 and most preferably by about 1:15 to about 1:20. If one or more silicones of the above formula are used, then the various variable substituents in the above formula may be different for the various silicone components present in the silicone mixture.

In a particularly preferred embodiment, the agent (a) is an amino-functional silicone polymer of the formula (Si-VII)

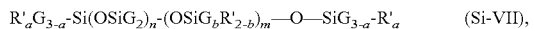  (Si-VII), wherein:
G is —H, a phenyl group, —OH, —O—$CH_3$, —$CH_3$, —O—$CH_2CH_3$, —$CH_2CH_3$, —O—$CH_2CH_2CH_3$, —$CH_2CH_2CH_3$, —O—$CH(CH_3)_2$, —$CH(CH_3)_2$, —O—$CH_2CH_2CH_2CH_3$, —$CH_2CH_2CH_2CH_3$, —O—$CH_2CH(CH_3)_2$, —$CH_2CH(CH_3)_2$, —O—$CH(CH_3)CH_2CH_3$, —$CH(CH_3)CH_2CH_3$, —O—$C(CH_3)_3$, —$C(CH_3)_3$; a stands for a number between 0 and 3, especially 0; b stands for a number between 0 and 1, especially 1, m and n are numbers whose sum (m+n) is between 1 and 2000, preferably between 50 and 150, where n preferably assumes values from 0 to 1999 and from 49 to 149 and m preferably assumes values from 1 to 2000, from 1 to 10, R' is a monovalent radical selected from
-Q-N(R")—$CH_2$—$CH_2$—N(R")$_2$
-Q-N(R")$_2$
-Q-N$^+$(R")$_3$A$^-$
-Q-N$^+$H(R")$_2$A$^-$
-Q-N$^+$H$_2$(R")A$^-$
-Q-N(R")—$CH_2$—$CH_2$—N$^+$R"H$_2$A$^-$, where each Q is a chemical bond, —$CH_2$—, —$CH_2$—$CH_2$—, —$CH_2CH_2CH_2$—, —$C(CH_3)_2$—, —$CH_2CH_2CH_2CH_2$—, —$CH_2C(CH_3)_2$—, —$CH(CH_3)CH_2CH_2$—, R" represents identical or different radicals selected from the group of —H, -phenyl, -benzyl, —$CH_2$—$CH(CH_3)Ph$, the $C_{1-20}$ alkyl radicals, preferably —$CH_3$, —$CH_2CH_3$, —$CH_2CH_2CH_3$, —$CH(CH_3)_2$, —$CH_2CH_2CH_2H_3$, —$CH_2CH(CH_3)_2$, —$CH(CH_3)CH_2CH_3$, —$C(CH_3)_3$, and A represents an anion preferably selected from chloride, bromide, iodide or methosulfate.

In a particularly preferred embodiment, the agent (a) comprises at least one amino-functional silicone polymer (a1) of the formula (Si-VIIa),

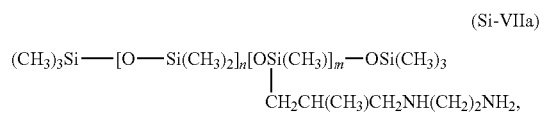

(Si-VIIa)

wherein m and n are numbers whose sum (m+n) is between 1 and 2000, preferably between 50 and 150, n preferably assuming values from 0 to 1999 and from 49 to 149, and m preferably assuming values from 1 to 2000, from 1 to 10.

According to the INCI declaration, these silicones are called trimethylsilylamodimethicones.

In a particularly preferred embodiment, the agent (a) comprises at least one amino-functional silicone polymer of the formula (Si-VIIb)

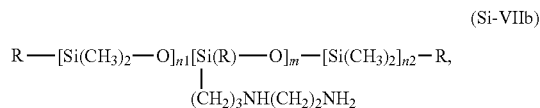

(Si-VIIb)

in which R represents —OH, —O—$CH_3$ or a —$CH_3$ group and m, n1 and n2 are numbers whose sum (m+n1+n2) is between 1 and 2000, preferably between 50 and 150, the sum (n1+n2) preferably assuming values from 0 to 1999 and from 49 to 149 and m preferably assuming values from 1 to 2000, from 1 to 10.

According to the INCI declaration, these amino-functionalized silicone polymers are called amodimethicones.

Regardless of which amino-functional silicones are used, agents (a) as contemplated herein are preferred which contain an amino-functional silicone polymer whose amine number is above 0.25 meq/g, preferably above 0.3 meq/g and above 0.4 meq/g. The amine number represents the milliequivalents of amine per gram of the amino-functional silicone. It can be determined by titration and expressed in the unit mg KOH/g.

Furthermore, the kit-of-parts in the first container may also comprise an agent (a) comprising a specific 4-morpholinomethyl-substituted silicone polymer (a1). This amino-functionalized silicone polymer comprises structural units of the formulae (SI-VIII) and of the formula (Si-IX)

(Si-VIII)

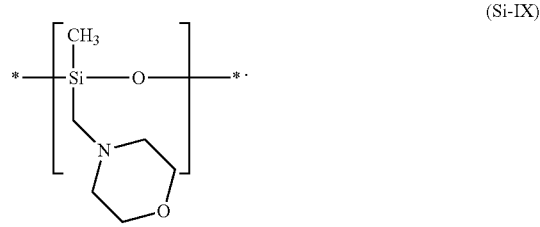

(Si-IX)

Corresponding 4-morpholinomethyl-substituted silicone polymers are described below.

A very particularly preferred amino-functionalized silicone polymer is known by the name of Amodimethicone/Morpholinomethyl Silsesquioxane Copolymer, which is known and commercially available from Wacker in the form of the raw material Belsil ADM 8301 E.

As a 4-morpholinomethyl-substituted silicone, for example, a silicone can be used which has structural units of the formulae (Si-VIII), (Si-IX) and (Si-X)

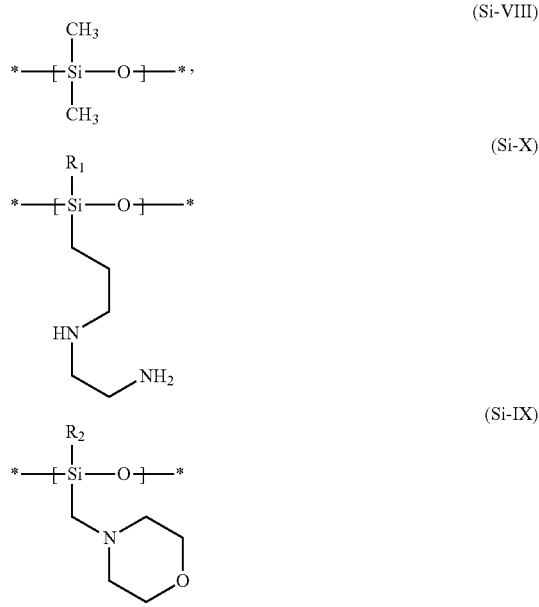

in which R1 is —CH$_3$, —OH, —OCH$_3$, —O—CH$_2$CH$_3$, —O—CH$_2$CH$_2$CH$_3$, or —O—CH(CH$_3$)$_2$; R2 is —CH$_3$, —OH, or —OCH$_3$.

Particularly preferred agent (a) as contemplated herein contain at least one 4-morpholinomethyl-substituted silicone of the formula (Si-XI)

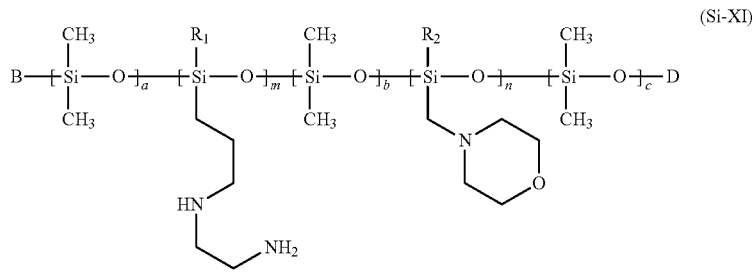

where
R1 is —CH$_3$, —OH, —OCH$_3$, —O—CH$_2$CH$_3$, —O—CH$_2$CH$_2$CH$_3$, or —O—CH(CH$_3$)$_2$;
R2 is —CH$_3$, —OH, or —OCH$_3$.
B represents a group —OH, —O—Si(CH$_3$)$_3$, —O—Si(CH$_3$)$_2$OH, —O—Si(CH$_3$)$_2$OCH$_3$,
D represents a group —H, —Si(CH$_3$)$_3$, —Si(CH$_3$)$_2$OH, —Si(CH$_3$)$_2$OCH$_3$, a, b and c stand independently for integers between 0 and 1000, with the condition a+b+c>0
m and n independently of each other stand for integers between 1 and 1000 with the proviso that
at least one of the conditions B=—OH or D=—H is fulfilled,
the units a, b, c, m and n are distributed statistically or blockwise in the molecule.

Structural formula (Si-XI) is intended to illustrate that the siloxane groups n and m do not necessarily have to be directly bonded to a terminal grouping B or D, respectively. Rather, in preferred formulas (Si-VI) a>0 or b>0 and in particularly preferred formulas (Si-VI) a>0 and c>0, i.e., the terminal grouping B or D is preferably attached to a dimethylsiloxy grouping. Also, in formula (Si-VI), the siloxane units a, b, c, m and n are preferably statistically distributed. The silicones used as contemplated herein represented by formula (Si-VI) can be trimethylsilyl-terminated (D or B=—Si(CH$_3$)$_3$), but they can also be dimethylsilylhydroxy-terminated on two sides or dimethylsilylhydroxy-terminated and dimethylsilylmethoxy-terminated on one side. Silicones particularly preferred in the context of the present disclosure are selected from silicones in which
B=—O—Si(CH$_3$)$_2$OH and D=—Si(CH$_3$)$_3$
B=—O—Si(CH$_3$)$_2$OH and D=—Si(CH$_3$)$_2$OH
B=—O—Si(CH$_3$)$_2$OH and D=—Si(CH$_3$)$_2$OCH$_3$
B=—O—Si(CH$_3$)$_3$ and D=—Si(CH$_3$)$_2$OH
B=—O—Si(CH$_3$)$_2$OCH$_3$ and D=—Si(CH$_3$)$_2$OH
to everyone. These silicones lead to exorbitant improvements in the hair properties of the hair treated with the agents of the present disclosure, and to a seriously improved protection in oxidative treatment.

The agent (a) used in the multicomponent packaging unit as contemplated herein is very preferably a concentrate comprising the amino-functionalized silicone polymer(s) (a1) in correspondingly excessive amounts. Particularly good dyeing results were obtained when the agent (a)—based on the total weight of the agent (a)—comprises one or more amino-functionalized silicone polymers (a1) in a total amount of from 5 to 100 wt. %, preferably from 25 to 100 wt. %, more preferably from 50 to 100 wt. % and very particularly preferably from 75 to 100 wt. %.

In the context of this embodiment, the amino silicones (a1) are either used in substance, or a solubilizer, diluent or carrier is added in lesser amounts to the amino silicone(s) (a1).

In another particularly preferred embodiment, the agent (a) comprises—based on the total weight of the agent (a)—one or more amino-functionalized silicone polymers (a1) in a total amount of from 5 to 100 wt. %, preferably from 25 to 100 wt. %, more preferably from 50 to 100 wt. % and very particularly preferably from 75 to 100 wt. %.

At a feed amount of about 100 wt. %, for example, the amino-functionalized silicone polymer (a1)—or also a mixture of amino silicones (a1)—can be used as a substance in the form of a concentrate. Before use, the agent (a) is then mixed with the agent (b).

Solvent in Agent (a)

As a solubilizer or diluent, a solvent may optionally additionally be used in the agent (a). For this reason, the agent (a) as contemplated herein may therefore additionally contain at least one solvent as an optional component.

Suitable solvents may include, for example, solvents selected from the group of 1,2-propylene glycol, 1,3-propylene glycol, ethylene glycol, 1,2-butylene glycol, dipropylene glycol, ethanol, isopropanol, diethylene glycol monoethyl ether, glycerol, phenoxyethanol and benzyl alcohol. The use of 1,2-propylene glycol is particularly preferred.

In another very particularly preferred embodiment, the agent (a) comprises at least one solvent selected from the group of 1,2-propylene glycol, 1,3-propylene glycol, ethylene glycol, 1,2-butylene glycol, dipropylene glycol, ethanol, isopropanol, diethylene glycol monoethyl ether, glycerol, phenoxyethanol and benzyl alcohol, very preferably 1,2-propylene glycol.

1,2-Propylene glycol is alternatively referred to as 1,2-propanediol and has CAS numbers 57-55-6 [(RS)-1,2-dihydroxypropane], 4254-14-2 [(R)-1,2-dihydroxypropane], and 4254-15-3 [(S)-1,2-dihydroxypropane]. Ethylene glycol is alternatively known as 1,2-ethanediol and carries CAS number 107-21-1. Glycerol is alternatively known as 1,2,3-propanetriol and carries CAS number 56-81-5. Phenoxyethanol has the Cas number 122-99-6.

All the solvents described previously are commercially available from various chemical suppliers, such as Aldrich or Fluka.

In a further preferred embodiment, the agent (a) comprises—based on the total weight of the agent (a)—one or more solvents in a total amount of 1.0 to 80.0 wt. %, preferably 2.0 to 50.0 wt. %, more preferably 3.0 to 30.0 wt. % and very particularly preferably 4.0 to 20.0 wt. %.

In another very particularly preferred embodiment, the agent (a) comprises—based on the total weight of the agent (a)—1.0 to 95.0 wt. %, preferably 2.0 to 15.0 wt. %, more preferably 3.0 to 15.0 wt. % and very particularly preferably 4.0 to 10.0 wt. % of 1,2-propylene glycol.

Packaging of the Agent (a)

As described above, the agent (a) may be a concentrate which preferably comprises the ingredient (b1) essential to the present disclosure as its main constituent.

If the composition additionally comprises at least one solvent, the two main components (a1) and solvent are preferably included in the agent (a).

Work carried out in the course of the present disclosure has further shown that, in order to achieve the best possible storage stability, it is advantageous to formulate the agent (a) in a low-water or water-free form.

In one embodiment, the agent (a) comprises—based on the total weight of the agent (a)—less than 10.0 wt. %, preferably less than 5.0 wt. %, further preferably less than 2.5 wt. % and very particularly preferably less than 1.0 wt. % of water.

In other words, in a further embodiment, the agent (a)—based on the total weight of the agent (a)—has a water content of between 0 and 10.0 wt. %, preferably between 0 and 5.0 wt. %, more preferably between 0 and 2.5 wt. % and very particularly preferably between 0 and 1.0 wt. %.

Further work has now shown that the homogeneity of the color result also depends on the agent into which the colorant compounds (i.e., the pigments) are incorporated. If the pigments were stored together with the amino silicone (a1) in the form of a premix and this was mixed with a cosmetic carrier formulation only shortly before application, the color intensity and wash fastness were significantly improved. However, it has been shown that this type of packaging is also associated with some disadvantages. If the mixture of amino silicone (a1) and pigment was stored for a longer time, a reaction of the two components with each other seemed to take place due to the storage time. In a low-water or anhydrous environment, this reaction was slowed down, but was nevertheless significant from storage times of several weeks. Therefore, poor miscibility of the amino silicon/pigment mixture with the carrier material was observed during the coloration of appropriately stored agents. As a result, very inhomogeneous color results were also obtained.

For this reason, it has further been found to be particularly preferable if the agent (a) itself does not contain any pigment or if these are used only in lesser amounts in the agent (a). Lesser amounts of pigment can, for example, be incorporated into the agent (a) to color it or give it a more aesthetic appearance.

In a further explicitly quite particularly preferred embodiment, the agent (a) comprises—based on the total weight of the agent (a)—one or more pigments in a total content of less than 0.1 wt. %, preferably less than 0.05 wt. % and very preferably less than 0.01 wt. %.

In other words, in a further explicitly quite particularly preferred embodiment, the agent (a)—based on the total weight of the agent (a)—has a pigment content which is between 0 and 0.1 wt. %, preferably between 0 and 0.05 wt. % and very particularly preferably between 0 and 0.01 wt. %.

It is explicitly quite preferred if the agent (a) does not contain any pigments.

Agent (b)

In a second container, the multi-component packaging unit as contemplated herein comprises agent (b). The container can be, for example, a sachet, a bottle, a can, ajar or also another container suitable for cosmetic formulations.

As a result of its content of water (b1) and buffer system (b2), the agent (b) represents a buffered formulation, which may be in the form of a gel or an emulsion, for example. As a result of its content of at least one coloring compound (b3), the agent (b) is a coloring gel, a coloring gel, a coloring shampoo, a coloring foam or otherwise a coloring cosmetically acceptable formulation.

Water Content (b1) in Agent (b)

In contrast to agent (a), agent (b) preferably comprises a high water content. It has been found that agents (b) which contain—based on the total weight of the agent (b)—50.0 to 98.0 wt. %, preferably 60.0 to 90.0 wt. %, further preferably 70.0 to 90.0 wt. % and most preferably 75.0 to 90.0 wt. % of water (b1) are particularly well suited for use.

In a further explicitly quite particularly preferred embodiment, the agent (b) comprises—based on the total weight of the agent (b)—50.0 to 98.0 wt. %, preferably 60.0 to 90.0 wt. %, further preferably 70.0 to 90.0 wt. % and very particularly preferably 75.0 to 90.0 wt. % of water (b1).

Buffer System (b2) in Agent (b)

As a second essential component of the present disclosure, the agent (b) of the kit-of-parts as contemplated herein comprises at least one buffer system (b2) comprising at least one inorganic or organic acid (b2-I) and at least one salt of this acid (b2-II).

A buffer or buffer system is usually understood to be a mixture of a weak or medium-strength acid (e.g., acetic acid) with a completely dissociated neutral salt of the same acid (e.g., sodium acetate). If some base or acid is added, the pH value hardly changes (buffering). The effect of the buffer substances included in a buffer solution is based on the scavenging reaction of hydrogen or hydroxide ions with the formation of weak acids or bases due to their dissociation equilibrium.

A buffer system can be formed from a mixture of an inorganic or organic acid and a corresponding salt of that acid.

Acids can be buffered by all salts of weak acids and strong bases, bases by salts of strong acids and weak bases. The strong hydrochloric acid (completely dissociated into ions) can be buffered, for example, by adding sodium acetate. According to the balance

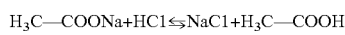

hydrochloric acid is converted by sodium acetate to the weak acetic acid with the formation of sodium chloride, which dissociates only to a small extent in the presence of an excess of sodium acetate. Buffers that are effective against both acids and bases are mixtures of weak acids and their salts.

Examples of buffer systems known from the literature are acetic acid/sodium acetate, boric acid/sodium borate, phosphoric acid/sodium phosphate and hydrogen carbonate/soda. The pH value of the agent (b) as contemplated herein is adjusted by adding an inorganic or organic buffer system (b2). For the purposes of the present disclosure, an inorganic buffer system (b2) is understood to be a mixture of an inorganic acid (b2-I) and its conjugate corresponding inorganic base (b2-II).

For the purposes of the present disclosure, an organic buffer system (b2) is understood to be a mixture of an organic acid (b2-I) and its conjugate corresponding base (b2-II). Due to the organic acid radical, the conjugate corresponding base of the organic acid (b2-II) is also organic. Here, the cation presents to neutralize the charge of the acid anion can be inorganic or organic.

Examples of inorganic acids (b2-I) are sulfuric acid ($H_2SO_4$), hydrochloric acid (HCl), and phosphoric acid ($H_3PO_4$). Phosphoric acid is a medium-strength acid that is particularly preferred.

A particularly well-suited inorganic acid (b2-I) is potassium dihydrogen phosphate Potassium dihydrogen phosphate has the molecular formula $KH_2PO_4$ and carries the CAS number 7778-77-0. Potassium dihydrogen phosphate has a molar mass of 136.09 g/mol. It is highly soluble in water (222 g/l at 20° C.) and reacts acidically in water. A 5% solution of potassium dihydrogen phosphate in water has a pH value of 4.4.

Another particularly suitable inorganic acid (b2-I) is sodium dihydrogen phosphate. Sodium dihydrogen phosphate has the molecular formula $NaH_2PO_4$ and carries the CAS numbers 7558-80-7 (anhydrate), 10049-21-5 (monohdate) and 13472-35-0 (dihydrate). The anhydrous sodium dihydrogen phosphate has a molar mass of 119.98 g/mol. Sodium dihydrogen phosphate reacts acidically in aqueous solution.

Particularly preferred as the corresponding salt of the above two acids (b2-II) are dipotassium hydrogen phosphate. Dipotassium hydrogen phosphate has the molecular formula $K_2HPO_4$ and carries the CAS numbers 7758-11-4 (anhydrous) and 16788-57-1 (trihydrate). The anhydrous dipotassium hydrogen phosphate has a molar mass of 174.18 g/mol. Dipotassium hydrogen phosphate reacts alkaline in aqueous solution.

Also particularly preferred as a corresponding salt of the above two acids (b2-II) are disodium hydrogen phosphate. Disodium hydrogen phosphate has the molecular formula $Na_2HPO_4$ and carries the CAS numbers 7558-79-4 (anhydrous), 10028-24-7 (dihydrate), 7782-85-6 (heptahydrate) and 10039-32-4 (dodecahydrate). Anhydrous disodium hydrogen phosphate has a molar mass of 141.96 g/mol. Disodium hydrogen phosphate reacts alkaline in aqueous solution.

Examples of organic acids (b2-I) are citric acid, succinic acid, tartaric acid, lactic acid, acetic acid, malic acid, malonic acid and maleic acid.

Examples of the corresponding salts of these organic acids (b2-II) are the sodium and potassium salts of citric acid, the sodium and potassium salts of succinic acid, the sodium and potassium salts of tartaric acid, sodium and potassium salts of lactic acid, sodium and potassium salts of acetic acid, sodium and potassium salts of malic acid, sodium and potassium salts of malonic acid and sodium and potassium salts of maleic acid.

To determine the effectiveness of a buffer, its buffer capacity can be used. A buffer capacity of 1 corresponds to a buffer solution whose pH value changes by one unit when 1 mol of acid or base is added per liter of buffer solution.

In the course of the work leading to the present disclosure, it has been found that agents (b).

had a particularly high buffer capacity when the acid (b2-I) and its corresponding salt (b2-II) were used in optimally matched molar ratios. In this context, it is particularly preferred if the inorganic or organic acid (b2-I) and the salt or salts of the inorganic or organic acid (b2) are used in a molar ratio (b2-I)/(b2-II) of from 1:15 to 15:1, preferably from 1:10 to 10:1, more preferably from 1:5 to 5:1 and very particularly preferably from 1:3 to 1:1.

In other words, it has been found to be most preferred when the acid (b2-I) and the salt(s) (b2-II) thereof are used either in equal total molar amounts, or when the salts (b2-II) are present in an up to threefold molar excess in the agent (b) relative to the acid (b2-I).

The basis for the calculation of the molar ratio (b2-I) to (b2-II)—i.e. (b2-I)/(b2-II)—is the total molar amount of the acid(s) (b2-I) included in the agent, which is set in relation to the total molar amount of all corresponding salts (b2-II) included in the agent.

Example 100 g of the agent as contemplated herein contain as buffer system (b2-I) 0.9 g phosphoric acid ($H_3PO_4$) and (b2-II) 1.5 g sodium dihydrogen phosphate ($NaH_2PO_4$) and 1.5 g potassium dihydrogen phosphate ($KH_2PO_4$)

Molar mass of phosphoric acid ($H_3PO_4$)=97.95 g/mol molar mass sodium dihydrogen phosphate ($NaH_2PO_4$)=119.92 g/mol Molar mass of potassium dihydrogen phosphate ($KH_2PO_4$)=136.032 g/mol 100 g of the agent as contemplated herein contain (b2-I) 0.00918 mol phosphoric acid (=9.2 mmol) and (b2-II) 0.0125 mol sodium dihydrogen phosphate (12.5 mmol) and 0.011 mol (11.0 mmol) potassium dihydrogen phosphate.

The molar ratio (b2-I)/(b2-II) on the agent is [(0.00918 mol)/(0.0125 mol+0.011 mol)]=.

[0.00918 mol/0.0235]=1:2.6

Example 100 g of the agent as contemplated herein contain as buffer system (b2-I) 0.35 g potassium dihydrogen phosphate and (b2-II) 0.73 g disodium hydrogen phosphate
molar mass of potassium dihydrogen phosphate ($KH_2PO_4$)=136.09 g/mol molar mass of disodium hydrogen phosphate ($Na_2HPO_4$)=141.96 g/mol
100 g of the agent as contemplated herein contain as buffer system (b2-I) 2.57 mmol potassium dihydrogen phosphate and (b2-II) 5.12 mmol disodium hydrogen phosphate The molar ratio (b2-I)/(b2-II) on average is [(2.57 mmol)/(5.12 mmol)]=1:1.99.

In a further particularly preferred embodiment, the agent (b) comprises the inorganic or organic acid(s) (b2-I) and the salt(s) of this acid(s) (b2-II) in a molar ratio (b2-I)/(b2-II) of from 1:15 to 15:1, preferably from 1:10 to 10:1, more preferably from 1:5 to 5:1 and very particularly preferably from 1:3 to 1:1.

In agent (b), for example, the following buffer systems (b2) can also be used:
Barbital acetate buffer according to Michaelis (pH 2.6 to 9.2)
Acetic acid-acetate buffer (pH 3.7 to 5.7)
Carbonic acid silicate buffer (pH 5.0 to 6.2; weakly acidic)
Phosphate buffer according to Sorensen (pH 5.4 to 8.0)
Phosphate citrate buffer according to McIlvaine
Carbonic acid bicarbonate system (pH 6.2 to 8.6; neutral)
Ammonia buffer: $NH_3+H_2O+NH_4Cl$ (pH 8.2 to 10.2)

The use of certain buffer systems has proved to be particularly preferred for solving the problem as contemplated herein. A buffer system (b2) which comprises at least one salt of the dihydrogen phosphate $H_2PO_4^-$(b2-I) and at least one salt of the hydrogen phosphate $HPO_4^{2-}$(b2-II) has proven to be particularly suitable, wherein said salt of dihydrogen phosphate is preferably selected from the group of sodium dihydrogen phosphate and potassium dihydrogen phosphate, and wherein said salt of hydrogen phosphate is preferably selected from the group of disodium hydrogen phosphate and dipotassium hydrogen phosphate.

In a further particularly preferred embodiment, agent (b) comprises a
(b2) buffer system comprising at least one salt of dihydrogen phosphate $H_2PO_4^-$(b2-I) and at least one salt of hydrogen phosphate $HPO_4^{2-}$(b2-II),
wherein said salt of dihydrogen phosphate is preferably selected from the group of sodium dihydrogen phosphate and potassium dihydrogen phosphate, and wherein said salt of hydrogen phosphate is preferably selected from the group of disodium hydrogen phosphate and dipotassium hydrogen phosphate.

Likewise, particularly good storage stability was obtained with a buffer system (b2), comprising succinic acid (b2-I) and a salt of succinic acid (b2-I), wherein the salt of succinic acid (b2-II) is preferably selected from the sodium salt of succinic acid and the potassium salt of succinic acid.

In a further particularly preferred embodiment, a multi-component packaging unit as contemplated herein comprises the agent (b) comprising
(b2) a buffer system comprising succinic acid (b2-I) and at least one salt of succinic acid (b2-II).

The pH value to which the agent (b) of the present disclosure is adjusted depends on the amount of acid or its salts used in the agent. It has been shown that satisfactory results could be obtained when a buffer system (b2) was used in the agent (b), which allowed the adjustment of a pH value of 6.0 to 8.0, preferably of 6.0 to 7.5, further preferably of 6.0 to 7.2 and most preferably of 6.0 to 7.0.

In a further particularly preferred embodiment, a multi-component packaging unit as contemplated herein wherein the agent (b) has a pH of from 6.0 to 8.0, preferably from 6.0 to 7.5, more preferably from 6.0 to 7.2, and most preferably from 6.0 to 7.0.

The pH values for the purposes of the present disclosure are pH values measured at a temperature of 22° C.

When mixing the agents (a) and (b), the preferably highly concentrated and low-water concentrate (a) is mixed with the actual colorant (b). During this mixing, the amino silicones (a1) are brought into contact with the pigments (b3) present in a buffered, aqueous environment, so that the previously described interaction of the amino silicones (a1) and pigments (b3) only starts from this moment of mixing. Surprisingly, it was observed that this type of finishing in the dyeing process leads to color results that are intense and washfast but are also exemplified by particularly good storage stability and reproducibility of the color result.

Colorant Compound (b3) in the Agent (b)

As a third essential component of the present disclosure, the agent (b) comprises at least one color-imparting compound (b3).

For the purposes of the present disclosure, colorant compounds are substances capable of imparting a coloration to the keratin material. Particularly well-suited colorant compounds can be selected from the group of pigments, direct-acting dyes, photochromic dyes and thermochromic dyes.

In a further preferred embodiment, the agent (b) comprises at least one colorant compound (b3) from the group comprising pigments, direct dyes, photochromic dyes and thermochromic dyes.

Explicitly quite particularly preferred, the agent (b) comprises at least one pigment (b3) as the coloring compound.

Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. A stir-fish is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, an agent (b) as contemplated herein comprises at least one color-imparting compound (b3) from the group of inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-comprising silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

As contemplated herein, colored pearlescent pigments are also particularly preferred color pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, the agent (b) comprises at least one coloring compound (b3) from the group of inorganic pigments, which is preferably selected from the group of colored metal oxides, metal hydroxides, metal oxide hydrates, silicates, metal sulfides, complex metal cyanides, metal sulfates, bronze pigments and/or from colored mica- or mica-based pigments coated with at least one metal oxide and/or a metal oxychloride.

In a further preferred embodiment, an agent (b) as contemplated herein comprises at least one colorant compound (b3) from the group of pigments selected from mica- or mica-based pigments reacted with one or more metal oxides selected from the group of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Examples of particularly suitable color pigments are commercially available under the trade names Rona®, Colorona®, Xirona®, Dichrona® and Timiron® from Merck, Ariabel® and Unipure® from Sensient, Prestige® from Eckart Cosmetic Colors and Sunshine® from Sunstar.

Particularly preferred color pigments with the trade name Colorona® are, for example:
Colorona Copper, Merck, MICA, CI 77491 (IRON OXIDES)
Colorona Passion Orange, Merck, Mica, CI 77491 (Iron Oxides), Alumina
Colorona Patina Silver, Merck, MICA, CI 77499 (IRON OXIDES), CI 77891 (TITANIUM DIOXIDE)
Colorona RY, Merck, CI 77891 (TITANIUM DIOXIDE), MICA, CI 75470 (CARMINE)
Colorona Oriental Beige, Merck, MICA, CI 77891 (TITANIUM DIOXIDE), CI 77491 (IRON OXIDES)
Colorona Dark Blue, Merck, MICA, TITANIUM DIOXIDE, FERRIC FERROCYANIDE
Colorona Chameleon, Merck, CI 77491 (IRON OXIDES), MICA
Colorona Aborigine Amber, Merck, MICA, CI 77499 (IRON OXIDES), CI 77891 (TITANIUM DIOXIDE)
Colorona Blackstar Blue, Merck, CI 77499 (IRON OXIDES), MICA
Colorona Patagonian Purple, Merck, MICA, CI 77491 (IRON OXIDES), CI 77891 (TITANIUM DIOXIDE), CI 77510 (FERRIC FERROCYANIDE)
Colorona Red Brown, Merck, MICA, CI 77491 (IRON OXIDES), CI 77891 (TITANIUM DIOXIDE)
Colorona Russet, Merck, CI 77491 (TITANIUM DIOXIDE), MICA, CI 77891 (IRON OXIDES)
Colorona Imperial Red, Merck, MICA, TITANIUM DIOXIDE (CI 77891), D&C RED NO. 30 (CI 73360)
Colorona Majestic Green, Merck, CI 77891 (TITANIUM DIOXIDE), MICA, CI 77288 (CHROMIUM OXIDE GREENS)
Colorona Light Blue, Merck, MICA, TITANIUM DIOXIDE (CI 77891), FERRIC FERROCYANIDE (CI 77510)
Colorona Red Gold, Merck, MICA, CI 77891 (TITANIUM DIOXIDE), CI 77491 (IRON OXIDES)
Colorona Gold Plus MP 25, Merck, MICA, TITANIUM DIOXIDE (CI 77891), IRON OXIDES (CI 77491)
Colorona Carmine Red, Merck, MICA, TITANIUM DIOXIDE, CARMINE
Colorona Blackstar Green, Merck, MICA, CI 77499 (IRON OXIDES)
Colorona Bordeaux, Merck, MICA, CI 77491 (IRON OXIDES)
Colorona Bronze, Merck, MICA, CI 77491 (IRON OXIDES)
Colorona Bronze Fine, Merck, MICA, CI 77491 (IRON OXIDES)
Colorona Fine Gold MP 20, Merck, MICA, CI 77891 (TITANIUM DIOXIDE), CI 77491 (IRON OXIDES)
Colorona Sienna Fine, Merck, CI 77491 (IRON OXIDES), MICA
Colorona Sienna, Merck, MICA, CI 77491 (IRON OXIDES)
Colorona Precious Gold, Merck, Mica, CI 77891 (Titanium dioxide), Silica, CI 77491 (Iron oxides), Tin oxide
Colorona Sun Gold Sparkle MP 29, Merck, MICA, TITANIUM DIOXIDE, IRON OXIDES, MICA, CI 77891, CI 77491 (EU)
Colorona Mica Black, Merck, CI 77499 (Iron oxides), Mica, CI 77891 (Titanium dioxide)
Colorona Bright Gold, Merck, Mica, CI 77891 (Titanium dioxide), CI 77491 (Iron oxides)
Colorona Blackstar Gold, Merck, MICA, CI 77499 (IRON OXIDES)

Other particularly preferred color pigments with the trade name Xirona® are for example:
Xirona Golden Sky, Merck, Silica, CI 77891 (Titanium Dioxide), Tin Oxide
Xirona Caribbean Blue, Merck, Mica, CI 77891 (Titanium Dioxide), Silica, Tin Oxide
Xirona Kiwi Rose, Merck, Silica, CI 77891 (Titanium Dioxide), Tin Oxide
Xirona Magic Mauve, Merck, Silica, CI 77891 (Titanium Dioxide), Tin Oxide.

In addition, particularly preferred color pigments with the trade name Unipure® are for example:
Unipure Red LC 381 EM, Sensient CI 77491 (Iron Oxides), Silica
Unipure Black LC 989 EM, Sensient, CI 77499 (Iron Oxides), Silica
Unipure Yellow LC 182 EM, Sensient, CI 77492 (Iron Oxides), Silica
Unipure Blue LC 689, CAS-No. 25689-005, Ammonium Iron(3+) Hexakis(cyano-C)ferrate(4−)

In a further embodiment, the agent (b) as contemplated herein may also comprise one or more colorant compounds (b3) from the group comprising organic pigments.

The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolo-pyorrole, indigo, thioindido, dioxazine and/or triarylmethane compounds.

Examples of particularly suitable organic pigments are carmine, quinacridone, phthalocyanine, sorghum, blue pigments with the Color Index numbers Cl 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In a further particularly preferred embodiment, the agent (b) comprises at least one colorant compound ($b_3$) from the group of organic pigments which is preferably selected from the group of carmine, quinacridone, phthalocyanine, sorghum, blue pigments having the Color Index numbers Cl 42090, CI 69800, CI 69825, CI 73000, CI 74100, CI 74160, yellow pigments having the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color paint. As contemplated herein, the term color lacquer means particles comprising a layer of absorbed dyes, the unit of particle and dye being insoluble under the above mentioned conditions. The particles can, for example, be inorganic substrates, which can be aluminum, silica, calcium borosilate, calcium aluminum borosilicate or even aluminum.

For example, alizarin color varnish can be used.

Due to their excellent light and temperature stability, the use of the above pigments in the agent (b) is particularly preferred. It is also preferred if the pigments used have a certain particle size. As contemplated herein, it is therefore advantageous if the at least one pigment has an average particle size $D_{50}$ of 1.0 to 50 µm, preferably 5.0 to 45 µm, preferably 10 to 40 µm, 14 to 30 µm. The mean particle size $D_{50}$, for example, can be determined using dynamic light scattering (DLS).

Particularly strong improvements in storage stability were observed when specific pigments (b3) were used in the agent (b) of the multicomponent packaging unit as contemplated herein. The very strongest effects were observed when agent (b) included at least one complex mitallcyanide as an inorganic pigment. Also, large effects were observed when the agent (b) included at least one organic pigment with the color index number CI 69800 and/or CI 19140.

For example, a corresponding complex mitallcyanide is Unipure Blue LC 689, which is also known as ammonium iron(3+) hexakis(cyano-C)ferrate(4−) and has CAS number 25869-00-5. An alternative name for this is Pigment Blue 27.

The organic pigment with the color index number CI 69800 can be obtained, for example, under the trade name Paliogen Blue L 6387. Alternative names are Pigment Blue 60 and Indanthron.

The organic pigment with the color index number CI 19140 can be purchased commercially under the trade name Unipure Yellow LC 125, for example. An alternative name for this is FD&C Yellow 5, Aluminum Lake.

The coloring compounds (b3), the coloring compounds from the group of pigments, represent the third ingredient of the agent (b) essential to the present disclosure. The pigment(s) is (are) used very preferably in certain ranges of amounts in the agent (b). Particularly satisfactory results were obtained when the agent (b)—based on the total weight of the agent (b)—included one or more pigments (b3) in a total amount of 0.05 to 10.0 wt. %, preferably 0.1 to 7.0 wt. %, more preferably 0.2 to 5.0 wt. % and most preferably 0.3 to 3.0 wt. %.

In another very particularly preferred embodiment, the agent (b) comprises—based on the total weight of the agent (b)—one or more pigments (b3) in a total amount of from 0.05 to 10.0 wt. %, preferably from 0.1 to 7.0 wt. %, more preferably from 0.2 to 5.0 wt. % and very particularly preferably from 0.3 to 3.0 wt. %.

As colorant compounds (b3), the agent (b) may also contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at 25° C. of more than 0.5 g/L and are therefore not to be regarded as pigments.

Preferably, the direct dyes within the meaning of the present disclosure have a solubility in water (760 mmHg) at 25° C. of more than 1.0 g/L.

Direct dyes can be divided into anionic, cationic and non-ionic direct dyes.

In a further embodiment, the agent (b) comprises at least one colorant compound (b3) from the group comprising anionic, nonionic and cationic direct dyes.

Suitable cationic direct dyes include Basic Blue 7, Basic Blue 26, HC Blue 16, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76.

As non-ionic direct dyes, non-ionic nitro and quinone dyes and neutral azo dyes can be used. Suitable non-ionic direct dyes are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1- methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]lbenzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethyl-amino-4-nitrophenol.

Anionic direct dyes are also called acid dyes. Acid dyes are direct dyes that have at least one carboxylic acid group (—COOH) and/or one sulphonic acid group (—SO$_3$H). Depending on the pH value, the protonated forms (—COOH, —SO$_3$H) of the carboxylic acid or sulphonic acid groups are in equilibrium with their deprotonated forms (—COO$^-$, —SO$_3^-$ present). The proportion of protonated forms increases with decreasing pH value. If direct dyes are used in the form of their salts, the carboxylic acid groups or sulphonic acid groups are present in deprotonated form and are neutralized with corresponding stoichiometric equivalents of cations to maintain electro neutrality. Inventive acid dyes can also be used in the form of their sodium salts and/or their potassium salts.

The acid dyes within the meaning of the present disclosure have a solubility in water (760 mmHg) at 25° C. of more than 0.5 g/L and are therefore not to be regarded as pigments. Preferably the acid dyes within the meaning of the present disclosure have a solubility in water (760 mmHg) at 25° C. of more than 1.0 g/L.

The alkaline earth salts (such as calcium salts and magnesium salts) or aluminum salts of acid dyes often have a lower solubility than the corresponding alkali salts. If the solubility of these salts is below 0.5 g/L (25° C., 760 mmHg), they do not fall under the definition of a direct dye.

An essential characteristic of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

In a further embodiment, the agent (b) comprises at least one anionic direct dye (b3) which is selected from the group of the nitrophenylenediamines, the nitroaminophenols, the azo dyes, the anthraquinone dyes, the triarylmethane dyes the xanthene dyes, the rhodamine dyes, the oxazine dyes and/or the indophenol dyes, the dyes from the abovementioned group each having at least one carboxylic acid group (—COOH), a sodium carboxylate group (—COONa), a potassium carboxylate group (—COOK), a sulfonic acid group (—SO$_3$H), a sodium sulfonate group (—SO$_3$Na) and/or a potassium sulfonate group (—SO$_3$K).

Suitable acid dyes may include, for example, one or more compounds selected from the following group: Acid Yellow 1 (D&C Yellow 7, Citronin A, Ext. D&C Yellow No. 7, Japan Yellow 403, CI 10316, COLIPA n° B001), Acid Yellow 3 (COLIPA n°:C 54, D&C Yellow N° 10, Quinoline Yellow, E104, Food Yellow 13), Acid Yellow 9 (CI 13015), Acid Yellow 17 (CI 18965), Acid Yellow 23 (COLIPA n° C. 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA n° C.015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodium-salt; Brown No. 201; RESORCIN BROWN; ACID ORANGE 24; Japan Brown 201; D & C Brown No. 1), Acid Red 14 (C.I.14720), Acid Red 18 (E124, Red 18; CI 16255), Acid Red 27 (E 123, CI 16185, C-Rot 46, Real red D, FD&C Red Nr.2, Food Red 9, Naphthol red S), Acid Red 33 (Red 33, Fuchsia Red, D&C Red 33, CI 17200), Acid Red 35 (CI C.I.18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red n° 106 Pontacyl Brilliant Pink), Acid Red 73 (CI 27290), Acid Red 87 (Eosin, CI 45380), Acid Red 92 (COLIPA n° C.53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet n° 2, C.I. 60730, COLIPA n° C.063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreenl), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black n° 401, Naphthalene Black 10B, Amido Black 10B, CI 20 470, COLIPA n° B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. 0.1 g of the anionic direct dye is placed in a beaker. A stir-fish is added. Then add 100 ml of water. This mixture is heated to 25° C. on a magnetic stirrer while stirring. It is stirred for 60 minutes. The aqueous mixture is then visually assessed. If there are still undissolved radicals, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1.0 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and sisulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trinatirum salt of 7-hydroxy-8-[(E)-(4-sulfonato-1-naphthyl)-diazenyl)]-1,3-naphthalene disulfonate and has an extremely high water solubility of more than 20 wt. %.

Acid Red 33 is the diantrium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than 10 g/L (25° C.).

Acid Blue 9 is the disodium salt of 2-({4[N-ethyl(3-sulfonatobenzyl]amino]phenyl}{14-[(N-ethyl(3-sulfonatobenzyl)imino]-2,5-cyclohexadien-1-ylidene}methyl)-benzenesulfonate and has a solubility in water of more than 20 wt. % (25° C.).

In a further embodiment, the agent (b) comprises at least one direct dye (b3) selected from the group of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The direct dye(s) can be used in different amounts in the agent (b), depending on the desired color intensity. Satisfactory results could be obtained if the agent (b)—based on the total weight of the agent (b)—comprises one or more direct dyes (b3) in a total amount of from 0.01 to 10.0 wt. %, preferably from 0.1 to 8.0 wt. %, more preferably from 0.2 to 6.0 wt. % and most preferably from 0.5 to 4.5 wt. %.

Furthermore, the agent (b) may also contain at least one photochromic or thermochromic dye as the coloring compound (b3).

Photochromic dyes are dyes that react to irradiation with UV light (sunlight or black light) with a reversible change in hue. In this process, the UV light changes the chemical structure of the dyes and thus their absorption behavior (photochromism).

Thermochromic dyes are dyes that react to temperature changes with a reversible change in hue. In this process, the change in temperature alters the chemical structure of the dyes and thus their absorption behavior (Thermochromism).

Agent (b) may contain—based on the total weight of agent (b)—one or more photochromic dyes (b3) in a total amount of from 0.01 to 10.0 wt. %, preferably from 0.1 to 8.0 wt. %, more preferably from 0.2 to 6.0 wt. % and most preferably from 0.5 to 4.5 wt. %

Agent (b) may contain—based on the total weight of agent (b)—one or more thermochromic dyes (b3) in a total amount of from 0.01 to 10.0 wt. %, preferably from 0.1 to 8.0 wt. %, more preferably from 0.2 to 6.0 wt. % and most preferably from 0.5 to 4.5 wt. %

Fat Components in the Agent (b)

Optionally, the agent (b) may also additionally contain at least one fat component. It has been found that the use of at least one fatty constituent results in the agent (b) being in the form of an emulsion, which allows particularly good and rapid mixing with the agent (a).

The fatty components are hydrophobic substances that can form emulsions in the presence of water, forming micelle systems.

For the purposes of the present disclosure, "fatty components" means organic compounds with a solubility in water at room temperature (22° C.) and atmospheric pressure (760 mmHg) of less than 1 wt. %, preferably less than 0.1 wt. %. The definition of fat constituents explicitly covers only uncharged (i.e., non-ionic) compounds. Fat components have at least one saturated or unsaturated alkyl group with at least 12 C atoms. The molecular weight of the fat constituents is a maximum of 5000 g/mol, preferably a maximum of 2500 g/mol and particularly preferably a maximum of 1000 g/mol. The fat components are neither polyoxyalkylated nor polyglycerylated compounds.

Very preferably, the fat components optionally included in the agent (b) are selected from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

In another very particularly preferred embodiment, the agent (b) comprises one or more fat constituents from the group comprising the $C_{12}$-$C_{30}$ fatty alcohols, the $C_{12}$-$C_{30}$ fatty acid triglycerides, the $C_{12}$-$C_{30}$ fatty acid monoglycerides, the $C_{12}$-$C_{30}$ fatty acid diglycerides and/or the hydrocarbons.

In this context, very particularly preferred fat constituents are understood to be constituents from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons. For the purposes of the present disclosure, only non-ionic substances are explicitly regarded as fat components. Charged compounds such as fatty acids and their salts are not considered to be fat components.

The $C_{12}$-$C_{30}$ fatty alcohols can be saturated, mono- or polyunsaturated, linear or branched fatty alcohols with 12 to 30 C atoms.

Examples of preferred linear, saturated $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, Cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidone alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

The preferred representatives for branched fatty alcohols are 2-octyl-dodecanol, 2-hexyl-dodecanol and/or 2-butyl-dodecanol.

By selecting particularly well-suited fat components, the polarity and viscosity of agent (b) can be optimally adjusted so that complete and rapid mixing is ensured when agents (a) and (b) are mixed. As a result of the high homogeneity of the application mixture prepared from (a) and (b), a particularly uniform color result can also be ensured.

In this context, it has been found that the use of at least one $C_{12}$-$C_{30}$ fatty alcohol in agent (b) creates an optimal emulsion system.

In one embodiment, particularly good results were obtained when the agent (b) comprises one or more $C_{12}$-$C_{30}$ fatty alcohols selected from the group of dodecan-1-ol (dodecyl alcohol, lauryl alcohol), Tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol), Behenyl alcohol (docosan-1-ol), (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), Gadoleyl alcohol ((9Z)-Eicos-9-en-1-ol), Arachidone alcohol ((5Z,8Z,11Z,14Z)-Eicosa-5,8,11,14-tetraen-1-ol), Erucyl alcohol ((13Z)-Docos-13-en-1-ol), Brassidyl alcohol ((13E)-docosen-1-ol) 2-octyl-dodecanol, 2-hexyl-dodecanol and/or 2-butyl-dodecanol.

In another very particularly preferred embodiment, the second agent (b) comprises one or more $C_{12}$-$C_{30}$ fatty alcohols selected from the group of
Dodecan-1-ol (dodecyl alcohol, lauryl alcohol),
Tetradecan-1-ol (tetradecyl alcohol, myristyl alcohol),
Hexadecan-1-ol (hexadecyl alcohol, cetyl alcohol, palmityl alcohol),
Octadecan-1-ol (octadecyl alcohol, stearyl alcohol),
Arachyl alcohol (eicosan-1-ol),
Heneicosyl alcohol (heneicosan-1-ol),
Behenyl alcohol (docosan-1-ol),
(9Z)—Octadec-9-en-1-ol (oleyl alcohol),
(9E)—Octadec-9-en-1-ol (elaidyl alcohol),
(9Z,12Z)—Octadeca-9,12-dien-1-ol (linoleyl alcohol),
(9Z,12Z,15Z)—Octadeca-9,12,15-trien-1-ol (linolenoyl alcohol),
Gadoleyl alcohol ((9Z)-Eicos-9-en-1-ol),
Arachidonic alcohol ((5Z,8Z,11Z,14Z)-Eicosa-5,8,11,14-tetraen-1-ol),
Erucyl alcohol ((13Z)-docos-13-en-1-ol),
Brassidyl alcohol ((13E)-docosen-1-ol),
2-Octyl-dodecanol,
2-hexyl dodecanol and/or
2-Butyl-dodecanol comprises.

It has been found to be quite preferable to use one or more $C_{12}$-$C_{30}$ fatty alcohols in quite specific ranges of amounts.

It is particularly preferred if the agent (b)—based on the total weight of the agent (b)—comprises one or more $C_{12}$-$C_{30}$ fatty alcohols in a total amount of from 2.0 to 50.0 wt. %, preferably from 3.0 to 30.0 wt. %, more preferably from 4.0 to 20.0 wt. %, still more preferably from 5.0 to 15.0 wt. % and most preferably from 5.0 to 10.0 wt. %.

Furthermore, as a very particularly preferred fat component, the agent (b) may also contain at least one $C_{12}$-$C_{30}$ fatty acid triglyceride, the $C_{12}$-$C_{30}$ fatty acid monoglyceride and/or $C_{12}$-$C_{30}$ fatty acid diglyceride. For the purposes of the present disclosure, a $C_{12}$-$C_{30}$ fatty acid triglyceride is understood to be the triester of the trivalent alcohol glycerol with three equivalents of fatty acid. Both structurally identical and different fatty acids within a triglyceride molecule can be involved in the formation of esters.

As contemplated herein, fatty acids are to be understood as saturated or unsaturated, unbranched or branched, unsubstituted or substituted $C_{12}$-$C_{30}$ carboxylic acids. Unsaturated fatty acids can be mono- or polyunsaturated. For an unsaturated fatty acid, its C—C double bond(s) may have the Cis or Trans configuration.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

The fatty acid triglycerides can also be of natural origin. The fatty acid triglycerides or mixtures thereof occurring in soybean oil, peanut oil, olive oil, sunflower oil, macadamia nut oil, moringa oil, apricot kernel oil, marula oil and/or optionally hardened castor oil are particularly suitable for use in the product as contemplated herein.

A $C_{12}$-$C_{30}$ fatty acid monoglyceride is understood to be the monoester of the trivalent alcohol glycerol with one equivalent of fatty acid. Either the middle hydroxy group of glycerol or the terminal hydroxy group of glycerol may be esterified with the fatty acid.

$C_{12}$-$C_{30}$ fatty acid monoglycerides are particularly suitable in which a hydroxyl group of glycerol is esterified with a fatty acid, the fatty acids being selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], or nervonic acid [(15Z)-tetracos-15-enoic acid].

A $C_{12}$-$C_{30}$ fatty acid diglyceride is the diester of the trivalent alcohol glycerol with two equivalents of fatty acid. Either the middle and one terminal hydroxy group of glycerol may be esterified with two equivalents of fatty acid, or both terminal hydroxy groups of glycerol are esterified with one fatty acid each. The glycerol can be esterified with two structurally identical fatty acids or with two different fatty acids.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

Satisfactory results were obtained when agent (b) included at least one $C_{12}$-$C_{30}$ fatty acid monoglyceride selected from the monoesters of glycerol with one equivalent of fatty acid selected from the group of dodecanoic acid (lauric acid), Tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), Petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z, 11Z,14Z)-icosa-5,8,11,14-tetraenoic acid] and/or nervonic acid [(15Z)-tetracos-15-enoic acid].

In another very particularly preferred embodiment, the second agent (b) comprises at least one $C_{12}$-$C_{30}$ fatty acid monoglyceride selected from the monoesters of glycerol with one equivalent of fatty acid from the group of dodecanoic acid, tetradecanoic acid, hexadecanoic acid, tetracosanoic acid, octadecanoic acid, eicosanoic acid and/or docosanoic acid.

With regard to the solution of the problem as contemplated herein, it has proved to be particularly preferable if the agent (b)—based on the total weight of the agent (b)—included one or more $C_{12}$-$C_{30}$ fatty acid mono-, $C_{12}$-$C_{30}$ fatty acid di- and/or $C_{12}$-$C_{30}$ fatty acid triglycerides in a total amount of 0.1 to 20.0 wt. %, preferably 0.3 to 15.0 wt. %, further preferably 0.5 to 10.0 wt. % and very particularly preferably 5.0 to 9.0 wt. %, preferably from 0.3 to 15.0 wt. %, more preferably from 0.5 to 10.0 wt. %, and most preferably from 5.0 to 9.0 wt. %.

In a very particularly preferred embodiment, the agent (b) comprises—based on the total weight of the agent (b)—one or more $C_{12}$-$C_{30}$ fatty acid mono-, $C_{12}$-$C_{30}$ fatty acid di- and/or $C_{12}$-$C_{30}$ fatty acid triglycerides in a total amount of 0.1 to 20.0 wt. %, preferably 0.3 to 15.0 wt. %, further preferably 0.5 to 10.0 wt. % and very particularly preferably 5.0 to 9.0 wt. %, preferably from 0.3 to 15.0 wt. %, more preferably from 0.5 to 10.0 wt. %, and most preferably from 5.0 to 9.0 wt. %.

The $C_{12}$-$C_{30}$ fatty acid mono-, $C_{12}$-$C_{30}$ fatty acid di- and/or $C_{12}$-$C_{30}$ fatty acid triglycerides can be used as the sole fat components in the agent (b). However, it is particularly preferred to incorporate at least one $C_{12}$-$C_{30}$ fatty acid mono-, $C_{12}$-$C_{30}$ fatty acid di- and/or $C_{12}$-$C_{30}$ fatty acid triglyceride in combination with at least one $C_{12}$-$C_{30}$ fatty alcohol into the agent (b).

Furthermore, as a very particularly preferred fat constituent, the agent (b) may also contain at least one hydrocarbon.

Hydrocarbons are compounds consisting exclusively of the atoms carbon and hydrogen with 8 to 80 C atoms. In this context, aliphatic hydrocarbons such as mineral oils, liquid paraffin oils (e.g., Paraffinum Liquidum or Paraffinum Perliquidum), isoparaffin oils, semi-solid paraffin oils, paraffin waxes, hard paraffin (Paraffinum Solidum), Vaseline and polydecenes are particularly preferred.

Liquid paraffin oils (Paraffinum Liquidum and Paraffinum Perliquidum) have proven to be particularly suitable in this context. Paraffinum Liquidum, also known as white oil, is the preferred hydrocarbon. Paraffinum Liquidum is a mixture of purified, saturated, aliphatic hydrocarbons, consisting of hydrocarbon chains with a C-chain distribution of 25 to 35 C-atoms.

Very particularly satisfactory results were obtained when the agent (b) included at least one hydrocarbon selected from the group of mineral oils, liquid kerosene oils, isoparaffin oils, semisolid kerosene oils, kerosene waxes, hard kerosene (Paraffinum solidum), petrolatum and polydecenes.

In another very particularly preferred embodiment, the agent (b) comprises at least one fatty constituent from the group of hydrocarbons.

It has been found to be particularly preferable to use one or more hydrocarbons in specific ranges of amounts in agent (b).

With regard to the solution of the problem as contemplated herein, it has proved to be quite particularly preferable if the agent (b)—based on the total weight of the agent (b)—included one or more hydrocarbons in a total amount of from 0.5 to 20.0 wt. %, preferably from 1.0 to 15.0 wt. %, more preferably from 1.5 to 10.0 wt. % and most preferably from 2.0 to 8.0 wt. %.

In another very particularly preferred embodiment, the agent (b) comprises—based on the total weight of the agent (b)—one or more hydrocarbons in a total amount of from 0.5 to 20.0 wt. %, preferably from 1.0 to 15.0 wt. %, more preferably from 1.5 to 10.0 wt. % and very particularly preferably from 2.0 to 8.0 wt. %.

Surfactants in the Agent (b)

As described above, it has proved preferable to prepare the agent (b) in the form of an emulsion. To further optimize the formation of the emulsion, it has proven particularly preferable to continue to use at least one surfactant in the agent (b).

Quite preferably, therefore, the agent (b) additionally comprises at least one surfactant.

In the context of a further particularly preferred embodiment, the agent (b) comprises at least one surfactant.

The term surfactants (T) refers to surface-active substances that can form adsorption layers on surfaces and interfaces or aggregate in bulk phases to form micelle colloids or lyotropic mesophases. A distinction is made between anionic surfactants consisting of a hydrophobic radical and a negatively charged hydrophilic head group, amphoteric surfactants, which carry both a negative and a compensating positive charge, cationic surfactants, which in addition to a hydrophobic radical have a positively charged hydrophilic group, and non-ionic surfactants, which have no charges but strong dipole moments and are strongly hydrated in aqueous solution.

In a very particularly preferred embodiment, the agent (b) comprises at least one nonionic surfactant.

Non-ionic surfactants contain, for example, a polyol group, a polyalkylene glycol ether group or a combination of polyol and polyglycol ether group as the hydrophilic group. Such links include Addition products of 2 to 50 mol ethylene oxide and/or 0 to 5 mol propylene oxide to linear and branched fatty alcohols with 6 to 30 C atoms, the fatty alcohol polyglycol ethers or the fatty alcohol polypropylene glycol ethers or mixed fatty alcohol polyethers, Addition products of 2 to 50 mol ethylene oxide and/or 0 to 5 mol propylene oxide to linear and branched fatty acids with 6 to 30 C atoms, the fatty acid polyglycol ethers or the fatty acid polypropylene glycol ethers or mixed fatty acid polyethers, Addition products of 2 to 50 mol ethylene oxide and/or 0 to 5 mol propylene oxide to linear and branched alkylphenols having 8 to 15 C atoms in the alkyl group, the alkylphenol polyglycol ethers or the alkyl polypropylene glycol ethers or mixed alkylphenol polyethers, with a methyl or $C_2$-$C_6$-alkyl radical end-group capped addition products of 2 to 50 moles of ethylene oxide and/or 0 to 5 moles of propylene oxide to linear and branched fatty alcohols with 8 to 30 C atoms, to fatty acids with 8 to 30 C atoms and to alkylphenols with 8 to 15 C atoms in the alkyl group, such as the grades available under the sales names Dehydol® LS, Dehydol® LT (Cognis), $C_{12}$-$C_{30}$ fatty acid mono- and diesters of addition products of 1 to 30 mol ethylene oxide to glycerol, Addition products of 5 to 60 mol ethylene oxide to castor oil and hardened castor oil, Polyol fatty acid esters, such as the commercial product Hydagen® HSP (Cognis) or Sovermol® grades (Cognis), alkoxylated triglycerides, alkoxylated fatty acid alkyl esters of the formula (Tnio-1)

$$R^1CO\text{—}(OCH_2CHR^2)_w OR^3 \qquad \text{(Tnio-1)}$$

in which $R^lCO$ is a linear or branched, saturated and/or unsaturated acyl radical having 6 to 22 carbon atoms, $R^2$ is hydrogen or methyl, $R^3$ is linear or branched alkyl radicals having 1 to 4 carbon atoms and w is numbers from 1 to 20, amine oxides, Hydroxy mixed ethers, as described for example in DE-OS 19738866, Sorbitan fatty acid esters and addition products of ethylene oxide to sorbitan fatty acid esters such as polysorbates, Sugar fatty acid esters and addition products of ethylene oxide to sugar fatty acid ester, Addition products of ethylene oxide to fatty acid alkanol-amides and fatty amines, Sugar tensides of the alkyl and alkenyl oligoglycoside type according to formula (E4-II), $$R^4O\text{-}[G]_p \qquad \text{(Tnio-2)}$$

in which $R^4$ is an alkyl or alkenyl radical comprising 4 to 22 carbon atoms, G is a sugar residue comprising 5 or 6 carbon atoms and p is a number of 1 to 10. They can be obtained by the relevant methods of preparative organic chemistry. The alkyl and alkenyl oligoglycosides can be derived from aldoses or ketoses with 5 or 6 carbon atoms, preferably glucose. The preferred alkyl and/or alkenyl oligoglycosides are thus alkyl and/or alkenyl oligoglucosides. The index number p in the general formula (Tnio-2) indicates the degree of oligomerization (DP), i.e. the distribution of mono- and oligoglycosides and stands for a number between 1 and 10. While p must always be an integer in the individual molecule and can assume the values p=1 to 6, the value p for a certain alkyl oligoglycoside is an analytically determined arithmetical quantity, which usually represents a fractional number. Preferably alkyl and/or alkenyl oligoglycosides with an average degree of oligomerization p of 1.1 to 3.0 are used. From an application technology point of view, those alkyl and/or alkenyl oligoglycosides are preferred whose degree of oligomerization is less than 1.7 and lies between 1.2 and 1.4. The alkyl or alkenyl radical $R^4$ can be derived from primary alcohols comprising 4 to 11, preferably 8 to 10 carbon atoms. Typical examples are butanol, caproic alcohol, caprylic alcohol, caprin alcohol and undecrylic alcohol as well as their technical mixtures, such as those obtained in the hydrogenation of technical fatty acid methyl esters or during the hydrogenation of aldehydes from Roelen's oxo synthesis. Preferred are alkyl oligoglucosides with a chain length of $C_8$-$C_{10}$ (DP=1 to 3), which are obtained as a preliminary step in the distillative separation of technical $C_8$-$C_{18}$ coconut-fatty alcohol and may be contaminated with less than 6 wt. % of $C_{12}$ alcohol, and alkyl oligoglucosides based on technical $C_{9/11}$ oxoalcohols (DP=1 to 3). The alkyl or alkenyl radical $R^{15}$ can also be derived from primary alcohols having 12 to 22, preferably 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and their technical mixtures, which can be obtained as described above. Preferred are alkyl oligoglucosides based on hardened $C_{12/14}$ coconut alcohol with a DP of 1 to 3.

Sugar surfactants of the fatty acid N-alkyl polyhydroxyalkylamide type, a nonionic surfactant of formula (Tnio-3)

$$R^5CO\text{—}NR^6\text{—}[Z] \qquad \text{(Tnio-3)}$$

in which $R^5CO$ is an aliphatic acyl radical comprising 6 to 22 carbon atoms, $R^6$ is hydrogen, an alkyl or hydroxyalkyl radical comprising 1 to 4 carbon atoms and [Z] is a linear or branched polyhydroxyalkyl radical comprising 3 to 12 carbon atoms and 3 to 10 hydroxyl groups. The fatty acid N-alkyl polyhydroxyalkylamides are known substances that can usually be obtained by reductive amination of a reducing sugar with ammonia, an alkylamine or an alkanolamine and subsequent acylation with a fatty acid, a fatty acid alkyl ester or a fatty acid chloride. The fatty acid N-alkyl polyhydroxy-alkylamides are preferably derived from reducing sugars with 5 or 6 carbon atoms, especially from glucose. The preferred fatty acid N-alkyl polyhydroxyalkylamides are therefore fatty acid N-alkylglucamides as represented by the formula (Tnio-4):

$$R^7CO\text{—}(NR^8)\text{—}CH_2\text{—}[CH(OH)]_4\text{—}CH_2OH \qquad \text{(Tnio-4)}$$

Preferably, glucamides of the formula (Tnio-4) are used as fatty acid-N-alkyl polyhydroxyalkylamides, in which $R^8$ represents hydrogen or an alkyl group and $R^7CO$ represents the acyl radical of caproic acid, caprylic acid, capric acid, Lauric acid, myristic acid, palmitic acid, palmoleic acid, stearic acid, isostearic acid, oleic acid, elaidic acid, petroselinic acid, linoleic acid, linolenic acid, arachidic acid, gadoleic acid, behenic acid or erucic acid or their technical mixtures. Particularly preferred are fatty acid N-alkyl glucamides of the formula (Tnio-4), which are obtained by reductive amination of glucose with methylamine and subsequent acylation with lauric acid or C12/14 coconut fatty acid or a corresponding derivative. Furthermore, polyhydroxyalkylamides can also be derived from maltose and palatinose.

The sugar surfactants may preferably be present in the agent used as contemplated herein in amounts of 0.1-20 wt. %, based on the total agent. Amounts of 0.5-15 wt. % are preferred and amounts of 0.5-7.5 wt. % are particularly preferred.

Other typical examples of nonionic surfactants are fatty acid amide polyglycol ethers, fatty amine polyglycol ethers, mixed ethers or mixed formals, protein hydrolysates (especially wheat-based vegetable products) and polysorbates.

The alkylene oxide addition products to saturated linear fatty alcohols and fatty acids, each with 2 to 30 moles of ethylene oxide per mole of fatty alcohol or fatty acid, and the sugar surfactants have proved to be preferred nonionic surfactants. Preparations with excellent properties are also obtained if they contain fatty acid esters of ethoxylated glycerol as non-ionic surfactants.

These connections are identified by the following parameters. The alkyl radical R comprises 6 to 22 carbon atoms and can be either linear or branched. Primary linear and in 2-position methyl-branched aliphatic radicals are preferred. Such alkyl radicals are for example 1-octyl, 1-decyl, 1-lauryl, 1-myristyl, 1-cytyl and 1-stearyl. Especially preferred are 1-octyl, 1-decyl, 1-lauryl, 1-myristyl. When so-called "oxo-alcohols" are used as starting materials, compounds with an odd number of carbon atoms in the alkyl chain predominate.

The compounds with alkyl groups used as surfactants can each be uniform substances. However, it is usually preferable to start from native plant or animal raw materials in the production of these substances, so that one obtains substance mixtures with different alkyl chain lengths depending on the respective raw material.

For surfactants which are products of the addition of ethylene and/or propylene oxide to fatty alcohols or derivatives of these addition products, both products with a "normal" homologue distribution and those with a narrowed homologue distribution can be used. By "normal" homologue distribution we mean mixtures of homologues obtained in the reaction of fatty alcohol and alkylene oxide using alkali metals, alkali metal hydroxides or alkali metal alcoholates as catalysts. Constricted homologue distributions are obtained, on the other hand, when, for example, hydrotalcites, alkaline earth metal salts of ether carboxylic acids, alkaline earth metal oxides, hydroxides or alcoholates are used as catalysts. The use of products with narrowed homologue distribution may be preferred.

Particularly satisfactory results were obtained when an agent (b) was used in the kit-of-parts as contemplated herein, which included at least one ethoxylated fatty alcohol with a degree of ethoxylation of 10 to 40.

In another very particularly preferred embodiment, the agent (b) comprises at least one nonionic surfactant of the formula (T-I),

(T-I)

wherein
Rb is a saturated or unsaturated, unbranched or branched $C_8$-$C_{24}$ alkyl group, preferably a saturated, unbranched $C_{16}$- to $C_{18}$ alkyl group, and
m an integer from 10 to 40, preferably an integer from 20 to 35, and particularly preferably the number 30.

A particularly well-suited non-ionic surfactant of this type is ceteareth-30. Ceteareth-30 is a mixture of cetyl alcohol and stearyl alcohol, each ethoxylated with 30 units of ethylene oxide. The mixture of cetyl alcohol and stearyl alcohol is called cetearyl alcohol. Ceteareth-30 has the CAS number 68439-49-6 and can be purchased, for example, under the trade name Eumulgin B3 from BASF.

The nonionic surfactants, in particular the nonionic surfactants of formula (T-I), are preferably used in the appropriate amount ranges in agent (b). Thus, based on the total weight of agent (b), agent (b) may contain one or more nonionic surfactants in a total amount of from 0.1 to 20 wt. %, preferably from 0.2 to 10 wt. %, more preferably from 0.3 to 5 wt. %, and most preferably from 0.4 to 2.5 wt. %.

Amino Silicones Not Used in the Agent (b)

For application to the keratin material, agents (a) and (b) are mixed to produce a ready-to-use staining agent.

As described above, the agent (a) is preferably the concentrate of an amino silicone (a1), which encounters the buffered formulation comprising the colorant compounds (i.e., the pigments) (b3) only shortly before use. Mixing initiates the reaction or interaction of the amino silicones (a1) with the pigments (b3), which under the conditions of use leads to conglomeration, accumulation or aggregation of (a1) and (b3) and in this way immobilizes the pigments on the surface of the keratin fibers.

To enable a homogeneous color result on the keratin fiber, it has been found essential in this context that this interaction of (a1) and (b3) is started only shortly before or during the dyeing process and that a common storage of (a1) and (b3) is avoided. For this reason, it has further been found to be quite particularly preferred if the agent (b) itself does not contain any amino silicones.

In another explicitly very particularly preferred embodiment, the total content of amino-functionalized silicone polymers in the agent (b)—based on the total weight of the agent (b)—is below 1.0 wt. %, preferably below 0.5 wt. %, more preferably below 0.1 wt. % and very particularly preferably below 0.01 wt. %.

In other words, in a further explicitly quite particularly preferred embodiment, the agent (b) comprises—based on the total weight of the agent (a)—one or more amino-functionalized silicone polymers in a total amount of from 0 to 1.0 wt. %, preferably from 0 to 0.5 wt. %, more preferably from 0 to 0.1 wt. % and very particularly preferably from 0 to 0.01 wt. %.

It is explicitly quite preferred if the agent (b) does not contain any amino-functionalized silicone polymers.

Further Optional Ingredients in the Agents (a) and/or (b)

In addition to the ingredients essential to the present disclosure already described, agents (a) and/or (b) may also contain other optional ingredients.

For example, the agent (a) may contain a film-forming polymer. The film-forming polymer may be selected, for example, from the group of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers, explicitly very particularly preferred polyvinylpyrrolidone (PVP).

Further suitable film-forming polymers can be selected from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

Film-forming polymers selected from the group of synthetic polymers, polymers obtainable by free-radical polymerization, or natural polymers have proven to be well suited.

Other particularly well-suited film-forming polymers can be selected from the homopolymers or copolymers of olefins, such as cycloolefins, butadiene, isoprene or styrene, vinyl ethers, vinyl amides, the esters or amides of (meth) acrylic acid having at least one $C_1$-$C_{20}$ alkyl group, an aryl group or a C2-C10 hydroxyalkyl group.

Other film-forming polymers may be selected from the homo- or copolymers of isooctyl (meth)acrylate; isononyl (meth)acrylate; 2-ethylhexyl (meth)acrylate; lauryl (meth) acrylate); isopentyl (meth)acrylate; n-butyl (meth)acrylate; isobutyl (meth)acrylate; ethyl (meth)acrylate; methyl (meth)

acrylate; tert-butyl (meth)acrylate; stearyl (meth)acrylate; hydroxyethyl (meth)acrylate; 2-hydroxypropyl (meth)acrylate; 3-hydroxypropyl (meth)acrylate; and/or mixtures thereof.

Further film-forming polymers may be selected from the homo- or copolymers of (meth)acrylamide; N-alkyl-(meth)acrylamides, in those with C2-C18 alkyl groups, such as N-ethyl-acrylamide, N-tert-butyl-acrylamide, 1e N-octylcrylamide; N-di(C1-C4)alkyl-(meth)acrylamide.

Other preferred anionic copolymers are, for example, copolymers of acrylic acid, methacrylic acid or their $C_1$-$C_6$ alkyl esters, as they are marketed under the INCI Declaration Acrylates Copolymers. A suitable commercial product is for example Aculyn® 33 from Rohm & Haas. Copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Very particularly preferred polymers on the market are, for example, Aculyn® 22 (Acrylates/Steareth-20 Me-thacrylate Copolymer), Aculyn® 28 (Acrylates/Beheneth-25 Methacrylate Copolymer), Structure 2001® (Acryla-tes/Steareth-20 Itaconate Copolymer), Structure 3001® (Acrylates/Ceteth-20 Itaconate Copolymer), Structure Plus® (Acrylates/Aminoacrylates C10-30 Alkyl PEG-20 Itaconate Copolymer), Carbopol® 1342, 1382, Ultrez 20, Ultrez 21 (Acrylates/C10-30 Alkyl Acrylate Crosspolymer), Synthalen W 2000® (Acrylates/Palmeth-25 Acrylate Copolymer) or the Rohme and Haas distributed Soltex OPT (Acrylates/C12-22 Alkyl methacrylate Copolymer).

The homo- and copolymers of N-vinylpyrrolidone, vinylcaprolactam, vinyl-(C1-C6)alkyl-pyrrole, vinyl-oxazole, vinyl-thiazole, vinylpyrimidine, vinylimidazole can be named as suitable polymers based on vinyl monomers.

Furthermore, the copolymers octylacrylamide/acrylates/butylaminoethyl-methacrylate copolymer, as commercially marketed under the trade names AMPHOMER® or LOVOCRYL® 47 by NATIONAL STARCH, or the copolymers of acrylates/octylacrylamides marketed under the trade names DERMACRYL® LT and DERMACRYL® 79 by NATIONAL STARCH are particularly suitable.

Suitable olefin-based polymers include homopolymers and copolymers of ethylene, propylene, butene, isoprene and butadiene.

In another version, block copolymers can be used as film-forming hydrophobic polymers, which comprise at least one block of styrene or the derivatives of styrene. These block copolymers can be copolymers that contain one or more other blocks in addition to a styrene block, such as styrene/ethylene, styrene/ethylene/butylene, styrene/butylene, styrene/isoprene, styrene/butadiene. Such polymers are commercially distributed by BASF under the trade name "Luvitol HSB".

In a further embodiment, the agent (a) and/or (b) comprises at least one film-forming polymer selected from the group of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinyl caprolactam copolymers, vinylpyrrolidone/vinyl formamide copolymers and/or vinylpyrrolidone/vinyl alcohol copolymers, the copolymers of acrylic acid, of copolymers of methacrylic acid, of homopolymers or copolymers of acrylic acid esters, of homopolymers or copolymers of methacrylic acid esters, of homopolymers or copolymers of acrylic acid amides, of homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

The film-forming polymer or polymers are preferably used in specific ranges of amounts in agents (a) and/or (b). In this context, it has proved particularly preferable for solving the problem as contemplated herein if the agent (b) comprises—based on the total weight of the agent (b)—one or more polymers in a total amount of from 0.1 to 25.0 wt. %, preferably from 0.2 to 20.0 wt. %, more preferably from 0.5 to 15.0 wt. % and very particularly preferably from 1.0 to 7.0 wt. %.

The agents may also contain one or more surfactants. The term surfactants refer to surface-active substances. A distinction is made between anionic surfactants consisting of a hydrophobic radical and a negatively charged hydrophilic head group, amphoteric surfactants, which carry both a negative and a compensating positive charge, cationic surfactants, which in addition to a hydrophobic radical have a positively charged hydrophilic group, and non-ionic surfactants, which have no charges but strong dipole moments and are strongly hydrated in aqueous solution.

Zwitterionic surfactants are those surface-active compounds which carry at least one quaternary ammonium group and at least one —$COO^{(-)}$— or —$SO_3^{(-)}$ group in the molecule. Particularly suitable zwitterionic surfactants are the so-called betaines such as the N-alkyl-N, N-dimethyl-ammonium-glycinate, for example the cocoalkyl-dimethyl-ammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Ampholytic surfactants are surface-active compounds which, apart from a $C_8$-$C_{24}$ alkyl or acyl group, contain at least one free amino group and at least one —COOH— or —$SO_3H$ group in the molecule and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to 24 C atoms in the alkyl group. Typical examples of amphoteric or zwitterionic surfactants are alkylbetaines, alkylamidobetaines, amino-propionates, amino-glycinate, imidazoliniumbetaines and sulfobetaines.

Particularly preferred ampholytic surfactants are N-cocoalkylaminopropionate, cocoacylaminoethylaminopropionate and $C_{12}$-$C_{18}$ acylsarcosine.

In addition, the agents may also contain at least one cationic surfactant. Cationic surfactants are surfactants, i.e., surface-active compounds, each with one or more positive charges. Cationic surfactants contain only positive charges. Usually, these surfactants are composed of a hydrophobic part and a hydrophilic head group, the hydrophobic part usually consisting of a hydrocarbon backbone (e.g., consisting of one or two linear or branched alkyl chains) and the positive charge(s) being in the hydrophilic head group. Examples of cationic surfactants are quaternary ammonium compounds which, as hydrophobic radicals, may carry one or two alkyl chains with a chain length of 8 to 28 C atoms, quaternary phosphonium salts substituted with one or more alkyl chains with a chain length of 8 to 28 C atoms or tertiary sulfonium salts.

Furthermore, the cationic charge can also be part of a heterocyclic ring (e.g., an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of 0.1 to 45 wt. %, preferably 1 to 30 wt. % and most preferably 1 to 15 wt. %—based on the total weight of the respective agent.

Furthermore, the agent as contemplated herein may also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with 12 to 20 C atoms in the alkyl group and up to 16 glycol ether groups in the molecule.

The anionic surfactants are used in a total quantity of 0.1 to 45 wt. %, preferably 1 to 30 wt. % and most preferably 1 to 15 wt. %—based on the total weight of the respective agent.

The agents may also contain other active ingredients, auxiliaries and additives, such as solvents; fatty ingredients such as $C_8$-$C_{30}$ fatty alcohols, $C_8$-$C_{30}$ fatty acid triglycerides, $C_8$-$C_{30}$ fatty acid monoglycerides, $C_8$-$C_{30}$ fatty acid diglycerides and/or hydrocarbons; polymers; structurants such as glucose, maleic acid and lactic acid, hair conditioning compounds such as phospholipids, for example lecitin and cephalins; perfume oils, dimethyl isosorbide and cyclodextrins; fiber structure-improving active ingredients, in particular mono-, di- and oligosaccharides such as glucose, galactose, fructose, fructose and lactose; dyes for coloring the product; anti-dandruff active ingredients such as piroctone olamine, zinc omadine and climbazole; amino acids and oligopeptides; protein hydrolysates on an animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts, and bisabolol; Polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; Fats and waxes such as fatty alcohols, beeswax, montan wax and kerosene; swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescing agents such as ethylene glycol mono- and distearate and PEG-3 distearate; and blowing agents such as propane-butane mixtures, $N_2O$, dimethyl ether, $CO_2$ and air.

The selection of these other substances will be made by the specialist according to the desired properties of the agents. Regarding other optional components and the quantities of these components used, explicit reference is made to the relevant manuals known to the specialist. The additional active ingredients and auxiliary substances are preferably used in the preparations as contemplated herein in quantities of 0.0001 to 25 wt. % each, 0.0005 to 15 wt. %, based on the total weight of the respective agent.

As previously described, however, the agent (a) particularly preferably consists of the ingredients (a1) and, if appropriate, alkalizing agent (a2). If the agent (a) should also contain any of the other optional ingredients described above, these are particularly preferably used in the agent (a) only in lesser amounts.

Process for Staining Keratinous Material

The multi-component packaging unit of the first present disclosure as contemplated herein is excellently suited for use in a process for coloring keratinic material, in particular human hair.

A second subject matter of the present application is therefore a method for coloring keratinous material, in particular human hair, comprising the following steps:

(1) Providing an agent (a), wherein the agent (a) comprises:
  (a1) at least one amino-functionalized silicone polymer, and
(2) Providing an agent (b), wherein the agent (b) comprises:
  (b1) Water and
  (b2) a buffer system comprising at least one inorganic or organic acid (b2-I) and at least one salt of this acid (b2-II), and
  (b3) at least one colorant compound,
(3) Preparing an application mixture by mixing agents (a) and (b)
(4) Applying the application mixture prepared in step (3) to the keratinous material,
(5) Exposing the application mixture applied in step (4) to the keratinous material; and
(6) Rinsing the application mixture with water, the agents (a) and (b) having already been disclosed in detail in the description of the first subject matter of the present disclosure.

In step (1) of the method as contemplated herein, agent (a) is provided. Preferably, the agent (a) is in a packaging unit or container and can be made available to the user in this way.

In step (2) of the method as contemplated herein, agent (b) is provided. This agent (b) is also preferably located in the container of the kit-of-parts and is made available to the user in this way.

In step (3) of the process as contemplated herein, a ready-to-use mixture is prepared by mixing agents (a) and (b).

In principle, different amounts of agent (a) can be mixed with agent (b), so that mixing ratios (a)/(b) of 1:400:400 to 400:1:1 are conceivable.

However, since the agent (a) is preferably a concentrate, it has proved particularly preferable to use the agent (a) in lesser amounts and to dilute these with comparatively higher amounts of the colorant (b).

For example, with a quantity ratio (a)/(b) of 1:120, 1 g of agent (a) can be mixed with 120 g of agent (b). As another example, with a quantity ratio (a)/(b) of 1:100, 1 g of agent (a) can be mixed with 100 g of agent (b). As another example, with a quantity ratio (a)/(b) of 1:15, 15 g of agent (a) can be mixed with 75 g of agent (b). As another example, with a quantity ratio (a)/(b) of 1:25, 4 g of agent (a) can be mixed with 100 g of agent (b).

Preferably, the application mixture prepared from (a) and (b) has a slightly acidic to slightly alkaline adjusted pH value. Very preferably, the application mixture has a pH value of 6.0 to 8.0.

In step (4) of the process as contemplated herein, the application mixture prepared in step (4) is applied to the keratinous material, which is very preferably human hair.

Preferably, the application mixture is applied to the keratin material (or to the hair) within a period of 1 to 120 minutes, preferably 1 to 60 minutes, further preferably 1 to 30 minutes, and most preferably 1 to 15 minutes after its preparation in step (3).

In a further preferred embodiment, a method as contemplated herein is exemplified by:
(4) Applying application mixture to the keratinous material within a period of from 1 to 120 minutes, preferably from 1 to 60 minutes, more preferably from 1 to 30 minutes, and most preferably from 1 to 15 minutes after its preparation in step (3).

In step (5) of the process as contemplated herein, the application mixture is allowed to act on the keratinous material after its application. In this context, different exposure times of, for example, 30 seconds to 60 minutes are conceivable.

However, a major advantage of the dyeing system as contemplated herein is that an intensive color result can be achieved even in short periods after short exposure times. For this reason, it is advantageous if the application mixture remains on the keratin material only for comparatively short periods of time after its application, from 30 seconds to 15 minutes, preferably from 30 seconds to 10 minutes, and particularly preferably from 1 to 5 minutes.

In a further preferred embodiment, a method as contemplated herein is exemplified by:
(5) Exposing the application mixture applied in step (5) to the keratinous material for a period ranging from 30 seconds to 15 minutes, preferably from 30 seconds to 10 minutes, and more preferably from 1 to 5 minutes Finally, after the application mixture has acted on the keratin material, it is rinsed out with water in step (6).

Here, in one embodiment, the application mixture can be washed out with water only, i.e., without the aid of an after-treatment agent or a shampoo. The use of a post-treatment agent or conditioner in step (6) is also conceivable in principle.

However, to solve the task as contemplated herein and to increase the ease of use, it has proved particularly preferable to rinse the application mixture in step (6) exclusively with water without the aid of a further after-treatment agent, without shampoo and without conditioner.

In a further preferred embodiment, a method as contemplated herein is exemplified by:
(6) Rinsing the application mixture with water only.

The method as contemplated herein comprises steps (1) to (6).

In step (1) the agent (a) is provided, step (2) comprises providing the agent (b). These three steps do not necessarily have to take place one after the other but can also run simultaneously.

Thus, step (1) may occur before step (2), steps (1) and (2) and (3) may occur simultaneously, or step (2) may occur before step (1).

For example, if agents (a) and (b) are provided to the user in a multicomponent packaging unit, three agents are provided at the same time, and it is up to the user to decide which agent to remove first from the packaging.

The preparation of an application mixture by mixing agents (a) and (b) in step (3) can only be performed after providing both agents (a) and (b) and. The application of the application mixture in step (4) can only take place after its preparation in step (3). Similarly, the application mixture in step (5) may be applied after it has been applied to the keratin material, and the rinsing of the application mixture in step (6) may be carried out after it has been applied in step (5).

Concerning the further preferred embodiments of the method as contemplated herein, mutatis mutantis what has been said about the multi-component packaging unit as contemplated herein applies.

EXAMPLES

1. Formulations

The following formulations were produced:

| Agent (a) | (a) |
|---|---|
| Dow Corning 2-8566 (Siloxanes and Silicones, 3-[(2-Aminoethyl)amino]-2-methylpropyl Me, Di-Me-Siloxane" | 2.0 g |
| Total amount of concentrate (a) | 2.0 g |

| Agent (b) | (bV1) Comparison | (bE1) Invention |
|---|---|---|
| Cetyl alcohol | 3.0 g | 3.0 g |
| Lorol techn. (C12-C18 fatty alcohols) | 3.0 g | 3.0 g |
| 1,2-propanediol | 10.0 g | 10.0 g |
| Phenoxyethanol | 0.8 g | 0.8 g |
| Ceteareth-30 (Cetearyl alcohol, ethoxylated 30 EO) | 1.5 g | 1.5 g |
| Potassium dihydrogen phosphate | — | 0.35 g |
| Disodium hydrogen phosphate | — | 0.72 g |
| Potassium hydroxide 50% aqueous solution | ad pH 9.5 | — |
| Unipure Yellow LC 125 (CI 19140) | 1.0 | 1.0 |
| Water | ad 98 g | ad 98 g |
| Total quantity carrier-base (b) | 98 g | 98 g |
| pH value | 9.5 | 6.5 |

| Agent (b) | (bV2) Comparison | (bE2) Invention |
|---|---|---|
| Cetyl alcohol | 3.0 g | 3.0 g |
| Lorol techn. (C12-C18 fatty alcohols) | 3.0 g | 3.0 g |
| 1,2-propanediol | 10.0 g | 10.0 g |
| Phenoxyethanol | 0.8 g | 0.8 g |
| Ceteareth-30 (Cetearyl alcohol, ethoxylated 30 EO) | 1.5 g | 1.5 g |
| Potassium dihydrogen phosphate | — | 0.35 g |
| Disodium hydrogen phosphate | — | 0.72 g |
| Potassium hydroxide 50% aqueous solution | ad pH 9.5 | — |
| Unipure Blue LC 689, CAS-No. 25689-005, Ammonium Iron(3+) Hexakis(cyano-C)ferrate(4−) | 1.0 | 1.0 |
| Water | ad 98 g | ad 98 g |
| Total quantity carrier-base (b) | 98 g | 98 g |
| pH value | 9.5 | 6.5 |

| Agent (b) | (bV3) Comparison | (bE3) Invention |
|---|---|---|
| Cetyl alcohol | 3.0 g | 3.0 g |
| Lorol techn. (C12-C18 fatty alcohols) | 3.0 g | 3.0 g |
| 1,2-propanediol | 10.0 g | 10.0 g |
| Phenoxyethanol | 0.8 g | 0.8 g |
| Ceteareth-30 (Cetearyl alcohol, ethoxylated 30 EO) | 1.5 g | 1.5 g |
| Potassium dihydrogen phosphate | — | 0.35 g |
| Disodium hydrogen phosphate | — | 0.72 g |
| Potassium hydroxide 50% aqueous solution | ad pH 9.5 | — |
| Paliogen Blue L 6385 (6,15-dihydro-5,9,14,18-anthrazinetetrone, Pigment blue 60, CI69800) | 1.0 | 1.0 |
| Water | ad 98 g | ad 98 g |
| Total agent (b) | 98 g | 98 g |
| pH value | 9.5 | 6.5 |

2. Storage

All formulations were placed in glass containers with screw caps and stored in a temperature-controlled warming cabinet at 40° C. for 6 weeks.

3. Application

The stored formulations were used to prepare the application mixtures (AWM) given in the following tables.

Each application mixture was tested on hair strands (Kerling, Euronatural hair white, liquor ratio: 1 g application mixture per g strand of hair). The application mixture was left to act for three minutes. Subsequently, the hair strand was thoroughly washed (1 minute) with water, dried, and then visually evaluated under the daylight lamp.

|  | AWM 1, comparison | AWM 2, Invention |
|---|---|---|
| Agent (a) | 2 g Agent (a) | 2 g Agent (a) |
| Agent (b) | 98 g Agent (bV1) | 98 g Agent (bE1) |
| Color result | faint yellow | intense yellow |

|  | AWM 3, comparison | AWM 4, Invention |
|---|---|---|
| Agent (a) | 2 g Agent (a) | 2 g Agent (a) |
| Agent (b) | 98 g Agent (bV2) | 98 g Agent (bE2) |
| Color result | colorless - light blue | intense dark blue |

|  | AWM 5, comparison | AWM 5, Invention |
|---|---|---|
| Agent (a) | 2 g Agent (a) | 2 g Agent (a) |
| Agent (b) | 98 g Agent (bV3) | 98 g Agent (bE3) |
| Color result | Almost colorless | dark blue |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A multicomponent packaging unit for coloring keratinous material comprising, separately assembled:
   a first container comprising an agent (a), wherein the agent (a) comprises:
   (a1) at least one amino-functionalized silicone polymer, and
   a second container containing an agent (b), wherein the agent (b) comprises:
   (b1) water and
   (b2) a buffer system comprising at least one inorganic or organic acid (b2-I) and at least one salt of the inorganic or organic acid (b2-II), and
   (b3) at least one color-imparting compound.

2. A multicomponent packaging unit according to claim 1, wherein the agent (a) comprises at least one amino-functionalized silicone polymer (a1) having at least one secondary amino group.

3. A multicomponent packaging unit according to claim 1, wherein the agent (a) comprises at least one amino-functionalized silicone polymer (a1) comprising at least one structural unit of the formula (Si amino),

(Si-Amino)

where
ALK1 and ALK2 independently represent a linear or branched $C_1$-$C_{20}$ divalent alkylene group.

4. A multicomponent packaging unit according to claim 1, wherein the agent (a) comprises at least one amino-functionalized silicone polymer (a1) comprising structural units of the formula (Si-I) and of the formula (Si-II)

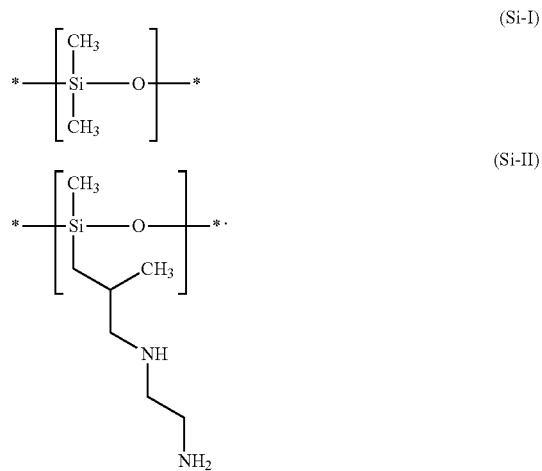

5. A multicomponent packaging unit according to claim 1, wherein the agent (a) comprises—based on the total weight of the agent (a)—one or more amino-functionalized silicone polymers (a1) in a total amount of from 5 to 100 wt. %.

6. A multicomponent packaging unit according to claim 1, wherein the agent (a) comprises—based on the total weight of the agent (a)—less than 10.0 wt. % of water.

7. A multicomponent packaging unit according to claim 1, wherein the agent (b) comprises—based on the total weight of the agent (b)—50.0 to 98.0 wt. % water (b1).

8. A multicomponent packaging unit according to claim 1, wherein the agent (b) comprises the inorganic or organic acid(s) (b2-I) and the salt(s) of said acid(s) (b2-II) in a molar ratio (b2-I)/(b2-II) of from 1:15 to 15:1.

9. A multicomponent packaging unit according to claim 1, wherein the agent (b) comprises
(b2) a buffer system comprising at least one salt of dihydrogen phosphate $H_2PO_4^-$ (b2-I) and at least one salt of hydrogen phosphate $HPO_4^{2-}$ (b2-II).

10. A multicomponent packaging unit according to claim 1, wherein the agent (b) comprises
(b2) a buffer system comprising succinic acid (b2-I) and at least one salt of succinic acid (b2-II).

11. A multicomponent packaging unit according to claim 1, wherein the agent (b) has a pH of from 6.0 to 7.0.

12. A multicomponent packaging unit according to claim 1, wherein the agent (b) comprises at least one colorant compound (b3) selected from the group consisting of pigments, direct dyes, photochromic dyes and thermochromic dyes.

13. A multicomponent packaging unit according to claim 1, wherein the agent (b) comprises at least one coloring compound (b3) selected from the group of inorganic pigments.

14. A multicomponent packaging unit according to claim 1, wherein the agent (b) comprises at least one colorant compound (b3) from the group of organic pigments.

15. A multicomponent packaging unit according to claim 1, wherein the agent (b) comprises—based on the total weight of the agent (b)—one or more pigments (b3) in a total amount of from 0.05 to 10.0 wt. %.

16. A process for dyeing keratinous material comprising the following steps:
(1) Providing an agent (a), wherein the agent (a) comprises:
    (a1) at least one amino-functionalized silicone polymer, and
(2) Providing an agent (b), wherein the agent (b) comprises:
    (b1) water and
    (b2) a buffer system comprising at least one inorganic or organic acid (b2-I) and at least one salt of this acid (b2-II), and
    (b3) at least one colorant compound,
(3) Preparing an application mixture by mixing agents (a) and (b),
(4) Applying the application mixture prepared in step (3) to the keratinous material,
(5) Exposing the application mixture applied in step (4) to the keratinous material; and
(6) Rising the application mixture with water.

17. A multicomponent packaging unit according to claim 1, wherein the agent (a) comprises at least one amino-functionalized silicone polymer (a1) comprising structural units of the formula (Si-I) and of the formula (Si-II)

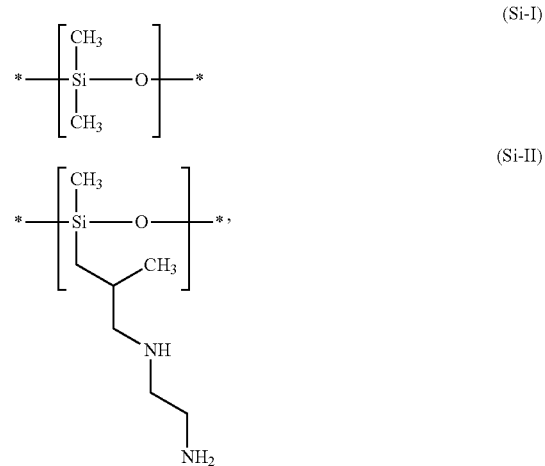

and
wherein the agent (b) comprises
(b2) a buffer system comprising at least one salt of dihydrogen phosphate $H_2PO_4^-$ (b2-I) and at least one salt of hydrogen phosphate $HPO_4^{2-}$ (b2-II).

18. A multicomponent packaging unit according to claim 17, wherein the agent (a) comprises—based on the total weight of the agent (a):
one or more amino-functionalized silicone polymers (a1) in a total amount of from 75 to 100 wt. %;
less than 1.0 wt. % of water.

19. A multicomponent packaging unit according to claim 17, wherein the agent (b) comprises—based on the total weight of the agent (b)—75.0 to 90.0 wt. % water (b1).

20. A multicomponent packaging unit according to claim 1, wherein the agent (b) comprises
(b2) a buffer system comprising at least one salt of dihydrogen phosphate $H_2PO_4^-$ (b2-I) and at least one salt of hydrogen phosphate $HPO_4^{2-}$ (b2-II),
wherein said salt of dihydrogen phosphate is selected from the group consisting of sodium dihydrogen phosphate and potassium dihydrogen phosphate, and wherein said salt of hydrogen phosphate is selected from the group consisting of disodium hydrogen phosphate and dipotassium hydrogen phosphate.

* * * * *

UNITED STATES PATENT AND TRADEMARK OFFICE
CERTIFICATE OF CORRECTION

PATENT NO. : 11,766,396 B2
APPLICATION NO. : 17/763177
DATED : September 26, 2023
INVENTOR(S) : Constanze Kruck et al.

It is certified that error appears in the above-identified patent and that said Letters Patent is hereby corrected as shown below:

In the Specification

Column 7, Line 4 change "3-[(2-aminoethy)pamino]" to --3-[(2-aminoethyl)amino]--.

Column 8, Line 41 change "M (Si-VI)" to --(Si-VI)--.

Column 13, Line 46 change "(b1)" to --(a1)--.

Column 21, Line 27 change "($b_3$)" to --(b3)--.

Column 24, Line 16 change "C.063" to --C063--.

Column 25, Line 9 change "{14-[(N-ethyl(3-sulfonatobenzyl)imino]-2" to --{4-[(N-ethyl(3-sulfonatobenzyl)imino]-2--.

Signed and Sealed this
Ninth Day of January, 2024

Katherine Kelly Vidal
*Director of the United States Patent and Trademark Office*